(12) United States Patent
Feng et al.

(10) Patent No.: US 9,610,239 B2
(45) Date of Patent: Apr. 4, 2017

(54) AQUEOUS SILICONE POLYETHER MICROEMULSIONS

(71) Applicant: Dow Corning Corporation, Midland, MI (US)

(72) Inventors: Qian Jane Feng, Midland, MI (US); Bethany K. Johnson, Midland, MI (US); Yihan Liu, Midland, MI (US)

(73) Assignee: DOW CORNING CORPORATION, Midland, MI (US)

( * ) Notice: Subject to any disclaimer, the term of this patent is extended or adjusted under 35 U.S.C. 154(b) by 0 days.

(21) Appl. No.: 14/421,162

(22) PCT Filed: Oct. 8, 2013

(86) PCT No.: PCT/US2013/063892
§ 371 (c)(1),
(2) Date: Feb. 12, 2015

(87) PCT Pub. No.: WO2014/058887
PCT Pub. Date: Apr. 17, 2014

(65) Prior Publication Data
US 2015/0216790 A1 Aug. 6, 2015

Related U.S. Application Data

(60) Provisional application No. 61/712,549, filed on Oct. 11, 2012.

(51) Int. Cl.
*C08G 77/14* (2006.01)
*A61K 8/894* (2006.01)
*A61K 8/49* (2006.01)
*A61Q 5/02* (2006.01)
*A61Q 5/06* (2006.01)
*A61Q 5/12* (2006.01)
*A61K 8/893* (2006.01)
*A61K 8/06* (2006.01)
*C08J 3/03* (2006.01)
*C08L 83/12* (2006.01)
*C08G 77/46* (2006.01)

(52) U.S. Cl.
CPC .............. *A61K 8/894* (2013.01); *A61K 8/068* (2013.01); *A61K 8/4993* (2013.01); *A61K 8/893* (2013.01); *A61Q 5/02* (2013.01); *A61Q 5/06* (2013.01); *A61Q 5/12* (2013.01); *C08J 3/03* (2013.01); *C08L 83/12* (2013.01); *A61K 2800/413* (2013.01); *C08G 77/14* (2013.01); *C08G 77/46* (2013.01); *C08J 2383/12* (2013.01)

(58) Field of Classification Search
CPC ........ A61K 8/894; A61K 8/4993; A61Q 5/02; A61Q 5/04; C08J 3/03; C08G 77/44; C08G 77/12
See application file for complete search history.

(56) References Cited

U.S. PATENT DOCUMENTS

| | | | |
|---|---|---|---|
| 4,122,029 A | 10/1978 | Gee et al. | |
| 4,620,878 A | 11/1986 | Gee | |
| 5,389,364 A | 2/1995 | Cifuentes et al. | |
| 5,409,695 A | 4/1995 | Abrutyn et al. | |
| 5,419,627 A | 5/1995 | Oldinski | |
| 5,443,760 A * | 8/1995 | Kasprzak | A61K 8/062 424/78.03 |
| 5,504,149 A | 4/1996 | Kosal | |
| 5,578,298 A | 11/1996 | Berthiaume et al. | |
| 5,683,625 A | 11/1997 | Berthiaume et al. | |
| 5,705,562 A | 1/1998 | Hill | |
| 5,707,613 A | 1/1998 | Hill | |
| 5,891,954 A | 4/1999 | Gee et al. | |
| 5,965,115 A * | 10/1999 | Bolich, Jr. | A61K 8/068 424/401 |
| 5,972,356 A | 10/1999 | Peffly et al. | |
| 5,985,294 A | 11/1999 | Peffly | |
| 6,147,038 A | 11/2000 | Halloran | |
| 6,153,569 A | 11/2000 | Halloran | |
| 6,180,117 B1 | 1/2001 | Berthiaume et al. | |
| 6,316,541 B1 | 11/2001 | Gee | |
| 6,998,424 B2 | 2/2006 | Feng et al. | |
| 7,465,669 B2 * | 12/2008 | Iyer | C23C 16/345 257/E21.17 |
| 9,126,163 B2 * | 9/2015 | Giessler-Blank | A01N 25/04 |
| 2003/0040571 A1 * | 2/2003 | Feng | A61K 8/068 524/837 |
| 2003/0143176 A1 | 7/2003 | Liu et al. | |
| 2005/0142087 A1 * | 6/2005 | Liu | A61K 8/06 424/66 |
| 2007/0190012 A1 * | 8/2007 | Feng | A61K 8/0208 424/70.12 |
| 2010/0112017 A1 * | 5/2010 | Mizutani | A61K 8/0212 424/401 |
| 2011/0142894 A1 * | 6/2011 | Watanabe | A61K 8/11 424/401 |
| 2011/0165206 A1 | 7/2011 | Liu et al. | |

(Continued)

* cited by examiner

Primary Examiner — Margaret Moore
(74) Attorney, Agent, or Firm — Timothy J. Troy

(57) ABSTRACT

Silicone polyether microemulsions are disclosed containing i) at least 20% by weight of a water immiscible dispersed phase comprising certain polydialkylsiloxane-polyoxyalkylene copolymers having 0.1 to 10 wt % ethylene oxide ($C_2H_4O$) groups, optionally a water immiscible silicone or hydrocarbon fluid, and ii) at least 5% by weight of an emulsifier. The silicone polyether microemulsions are optically transparent and have an average particle size of less than 100 nanometers. They may be used in a variety of personal care product formulations. In particular, the silicone polyether microemulsions may be used to prepare "clear" personal care products.

14 Claims, 2 Drawing Sheets

AQUEOUS SILICONE POLYETHER MICROEMULSIONS

CROSS-REFERENCE TO RELATED APPLICATIONS

This application is a national stage entry of International Patent Application No. PCT/US2013/063892, filed Oct. 8, 2013, which claims priority to and all the advantages of U.S. Provisional Patent Application No. 61/712,549, filed Oct. 8, 2012, the contents of each of which are incorporated herein by reference in their entirety.

BACKGROUND

Silicone polyethers are commonly known in the art for their use as surfactants. They are also typically used as additives or co-emulsifiers in aqueous dispersions. For example, certain silicone polyethers such as polydialkylsiloxane-polyoxyalkylene copolymers have been used as emulsifiers for various aqueous silicone emulsions. The relative amounts of the polydialkylsiloxane and polyoxyalkylene components in the copolymer may determine the emulsifying properties of the copolymer in a somewhat analogous manner as HLB values for organic nonionic surfactants containing polyoxyethylene as the hydrophilic group. Very often, if a hydrophobic silicone polyether is desired to be delivered as the oil phase in an emulsion, it tends to form a water-in-silicone polyether emulsion. Thus, there is a need to identify aqueous emulsions having a dispersed phase of silicone polyethers. There is a further need to identify such emulsions where the average particle size of the dispersed silicone polyether phase is less than 100 nanometers which may be considered as microemulsions.

BRIEF SUMMARY OF THE INVENTION

The present inventors have discovered certain silicone polyethers that form microemulsions. In particular, the present silicone polyethers are dispersed within the microemulsion composition having an average particle size of less than 100 nanometers. As such, the microemulsions are essentially clear and/or transparent to visible light.

The present silicone polyether microemulsions comprise:
i) at least 20% by weight of a water immiscible dispersed phase comprising:
A) a polydialkylsiloxane-polyoxyalkylene copolymer having the average formula:

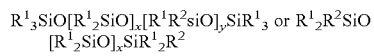
$R^1{}_3SiO[R^1{}_2SiO]_x[R^1R^2SiO]_ySiR^1{}_3$ or $R^1{}_2R^2SiO[R^1{}_2SiO]_xSiR^1{}_2R^2$ wherein
x ranges from 50 to 1000,
y ranges from 1 to 50,
$R^1$ is an alkyl group containing 1 to 6 carbon atoms,
$R^2$ is a polyoxyalkylene group having the average formula:

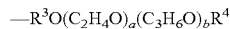
$—R^3O(C_2H_4O)_a(C_3H_6O)_bR^4$ wherein
a is greater than 4,
b ranges from 0 to 30,
$R^3$ is a divalent hydrocarbon group containing 2 to 12 carbon atoms,
$R^4$ is hydrogen, $R^1$, or an acetyl group,
with the proviso that the polydialkylsiloxane-polyoxyalkylene copolymer contains 0.1 to 10 wt % ethylene oxide ($C_2H_4O$) groups, B) optionally, a water immiscible silicone or hydrocarbon fluid, and
ii) at least 5% by weight of
C) an emulsifier selected from an anionic surfactant, a cationic surfactant, a nonionic surfactant, or a combination thereof, wherein
the silicone polyether microemulsion is optically transparent and has an average particle size of less than 100 nanometers.

The present microemulsions may be used in a variety of personal care product formulations. In particular, the silicone polyether microemulsions may be used to prepare "clear" personal care products.

DETAILED DESCRIPTION OF THE INVENTION

Figure 1:
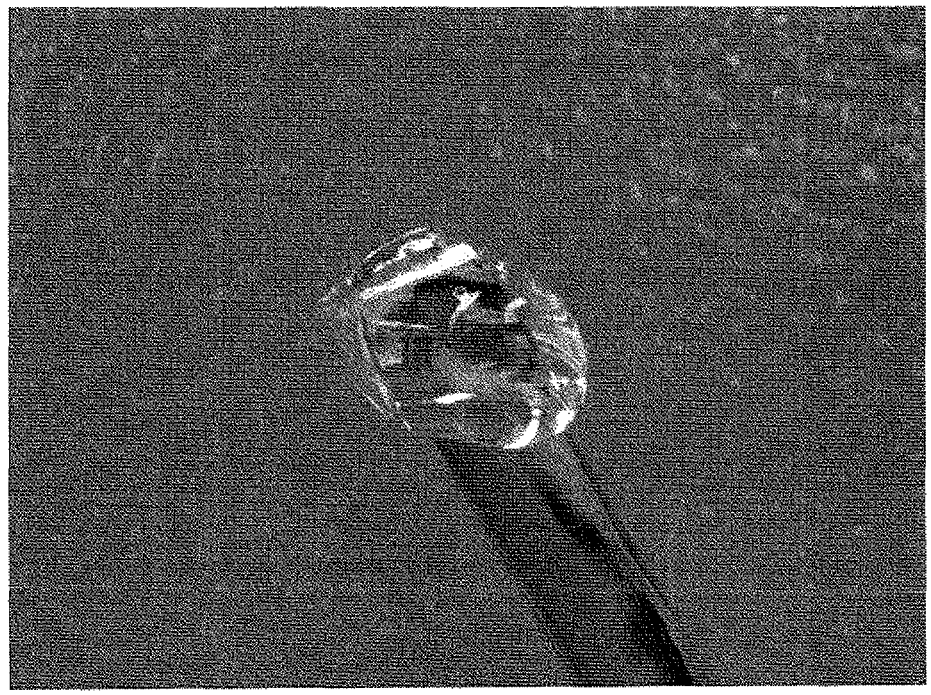
FIG. 1 is a first photo of the gel like behaviour of a clear high solids microemulsion composition (representative of Example 3)
Figure 2:
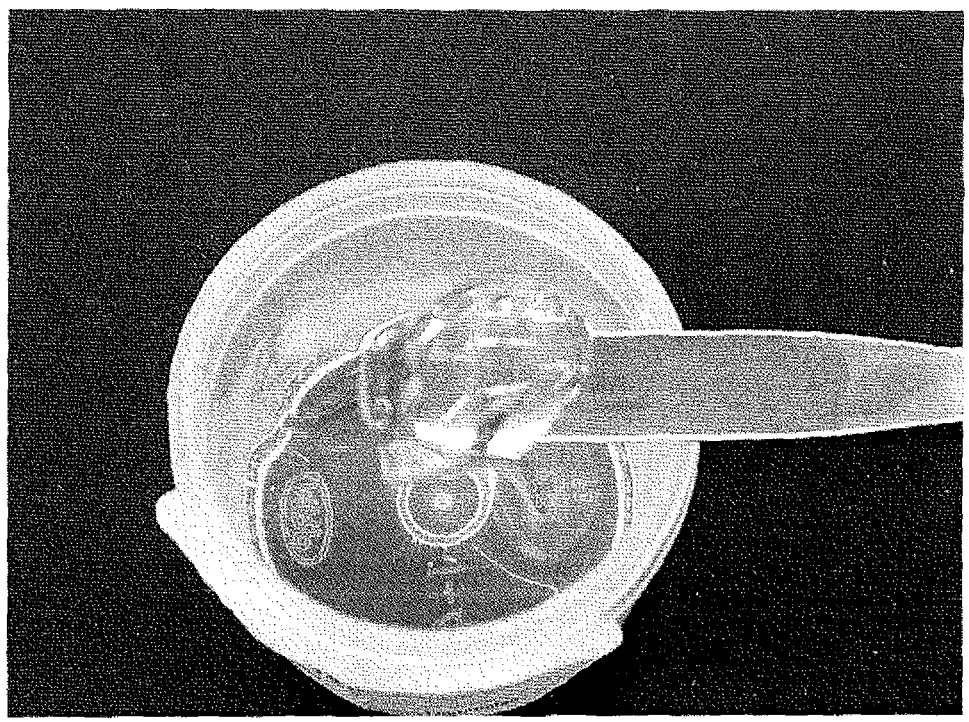
FIG. 2 is a second photo of the gel like behaviour of a clear high solids microemulsion composition (representative of Example 3)

The present disclosure relates to aqueous microemulsions of certain silicone polyethers and microemulsions of these silicone polyethers in combination with water immiscible organic or silicone fluids.

As used herein, microemulsion refers to single-phase or multiple-phase emulsions that are essentially optically clear or translucent. The "oil" phase or dispersed phase in the present microemulsions contains the silicone polyethers as described below, and/or a combination of these silicone polyethers with water immiscible organic fluids, silicone fluids, or a combination thereof. In the case of a single-phase microemulsion, the system is homogeneous and may be considered thermodynamically stable. Single-phase microemulsion can take the form of oil-swollen micelles in water (oil-in-water microemulsion) or water-swollen micelles in oil (water-in-oil microemulsion), or bi-continuous microemulsions. In the case of a multiple-phase emulsion (that is optically clear or translucent but the clarity is not due to match in the index of refraction of the different phases), the emulsion contains dispersed droplets that are smaller than the visible wavelength. The microemulsion according to the present disclosure includes all three forms of the single-phase microemulsions as well as multiple-phase emulsions of the oil droplet-in-water kind, in the latter case, the oil droplet being smaller than 100 nanometer. The present microemulsions invention may be further diluted in water to any arbitrary ratio and still retain its original optical clarity without phase separation.

The present microemulsions contain at least 20% by weight of a water immiscible dispersed phase, alternatively the microemulsion contains at least 30% by weight of the water immiscible dispersed phase, alternatively the microemulsion contains at least 40% by weight of the water immiscible dispersed phase, alternatively the microemulsion contains at least 50% by weight of the water immiscible dispersed phase or alternatively the microemulsion contains at least 60% by weight of the water immiscible dispersed phase.

The water immiscible dispersed phase comprises component A) a polydialkylsiloxane-polyoxyalkylene copolymer, and optionally component B) a water immiscible silicone or hydrocarbon fluid. Components A) and B) are described below. In one embodiment, the water immiscible dispersed phase consists essentially of component A) a polydialkylsiloxane-polyoxyalkylene copolymer, and optionally component B) a water immiscible silicone or hydrocarbon fluid. Alternatively, the water immiscible dispersed phase consists of component A) a polydialkylsiloxane-polyoxyalkylene copolymer, and optionally component B) a water immiscible silicone or hydrocarbon fluid.

A) The Polydialkylsiloxane-Polyoxyalkylene Copolymer

Component A) in the present microemulsions is a polydialkylsiloxane-polyoxyalkylene copolymer having the average formula:

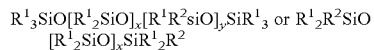
$$R^1{}_3SiO[R^1{}_2SiO]_x[R^1R^2SiO]_ySiR^1{}_3 \text{ or } R^1{}_2R^2SiO[R^1{}_2SiO]_xSiR^1{}_2R^2$$

wherein
x ranges from 50 to 1000,
y ranges from 1 to 50,
$R^1$ is an alkyl group containing 1 to 6 carbon atoms,
$R^2$ is a polyoxyalkylene group having the average formula:

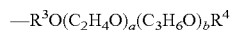
$$-R^3O(C_2H_4O)_a(C_3H_6O)_bR^4$$

wherein
a is greater than 4,
b may vary from 0 to 30,
$R^3$ is a divalent hydrocarbon group containing 2 to 12 carbon atoms,
$R^4$ is hydrogen,
$R^1$, or an acetyl group,
with the proviso that the polydialkylsiloxane-polyoxyalkylene copolymer contains 0.1 to 10 wt % ethylene oxide ($C_2H_4O$) groups.

The polydialkylsiloxane-polyoxyalkylene is a silicone polyether and may be selected from two general types. In one embodiment, the silicone polyether is a polydialkylsiloxane-polyoxyalkylene having the average formula $R^1{}_3SiO[R^1{}_2SiO]_x[R^1R^2SiO]_ySiR^1{}_3$. These silicone polyethers are often described as "rake type" silicone polyethers because of their geometry of a predominately linear siloxane chain having pendant polyether groups. In a second embodiment, the silicone polyether is a polydialkylsiloxane-polyoxyalkylene having the average formula $R^1{}_2R^2SiO[R^1{}_2SiO]_xSiR^1{}_2R^2$. These silicone polyethers are often described as "ABA" silicone polyethers because of their geometric structure of a predominately linear siloxane chain that is end-blocked with a polyether group.

The subscript "x" in the silicone polyether formulae above represents the number of dialkylsiloxy units in the polydialkylsiloxane and may vary from 50 to 1000, alternatively from 90 to 500, alternatively from 205 to 500, alternatively from 300 to 500, or alternatively from 350 to 450.

The subscript "y" in the silicone polyether formula above represents the number of disiloxy units in the polydialkylsiloxane-polyoxyalkylene containing a $R^2$ substitute and may vary from 1 to 50, alternatively from 1 to 20, or alternatively from 1 to 10.

$R^2$ in the above formulae is a polyoxyalkylene group having the average formula:

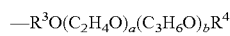
$$-R^3O(C_2H_4O)_a(C_3H_6O)_bR^4$$

wherein
the subscript "a" is greater than 4, alternatively a may vary from 4 to 30, alternatively from 4 to 15, or alternatively from 4 to 10,
the subscript "b" may vary from 0 to 30, alternatively from 0 to 20, or alternatively from 0 to 10.
$R^3$ is a divalent hydrocarbon group containing 2 to 12 carbon atoms, alternatively $R^3$ contains 2 to 6 carbon atoms, alternatively $R^3$ is propylene, or isobutylene, alternatively $R^3$ is propylene.
$R^4$ is hydrogen,
$R^1$, or an acetyl ($CH_3C(O)$—) group.

The present silicone polyethers contain a polyoxyalkylene moiety which is predominately a polyoxyethylene chain as designated by $(C_2H_4O)_a$ in the above formula (represented as EO in the examples). The polyoxyalkylene group comprises predominately oxyethylene units ($C_2H_4O$), but may also contain oxypropylene units as designated by ($C_3H_6O$) in the above formula (represented as PO in the examples), oxybutylene units ($C_4H_8O$), or mixtures thereof. When the polyoxyalkylene group comprises a mixture of ($C_2H_4O$), ($C_3H_6O$), and/or ($C_4H_8O$) units, the oxyalkylene groups are typically randomized with the group but can also be blocked. The polyoxyalkylene group comprises a sufficient amount of polyoxyethylene units to provide the polydialkylsiloxane-polyoxyalkylene copolymer with 0.1 to 10 wt % ethylene oxide ($C_2H_4O$) groups, alternatively with 0.1 to 8 wt % ethylene oxide, alternatively with 0.2 to 6 wt % ethylene oxide, or alternatively with 0.4 to 5 wt % ethylene oxide.

In one embodiment, the polydialkylsiloxane-polyoxyalkylene (component A) is insoluble in water and is not surface active, i.e., it is not a surfactant. It does not form any self-assembled structure with water such as micelles or liquid crystals or vesicles like some of the hydrophilic and smaller counter-parts do.

Any method known in the art for preparing silicone polyethers may used to prepare the polydialkylsiloxane-polyoxyalkylenes useful as component A) in the present microemulsions. Alternatively, the polydialkylsiloxane-polyoxyalkylenes useful as component A) may be prepared by reacting:

a) an organohydrogensiloxane copolymer having the average formula:

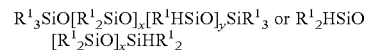
$$R^1{}_3SiO[R^1{}_2SiO]_x[R^1HSiO]_ySiR^1{}_3 \text{ or } R^1{}_2HSiO[R^1{}_2SiO]_xSiHR^1{}_2$$

wherein
x ranges from 50 to 1000,
y ranges from 1 to 50,
$R^1$ is an alkyl group containing 1 to 6 carbon atoms,
b) a polyoxyalkylene having the average formula:

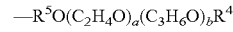
$$-R^5O(C_2H_4O)_a(C_3H_6O)_bR^4$$

wherein
a is greater than 4,
b ranges from 0 to 30,
$R^3$ is a divalent hydrocarbon group containing 2 to 12 carbon atoms,
$R^4$ is hydrogen,
$R^1$, or an acetyl group,
$R^5$ is an unsaturated aliphatic hydrocarbon group containing 2 to 12 carbon atoms, and
c) a hydrosilylation catalyst.

The polyoxyalkylene useful as component b) can be any polyoxyalkylene that is terminated at one molecular chain end with an unsaturated aliphatic hydrocarbon group containing 2 to 12 carbon atoms. The polyoxyalkylene may result from the polymerization of ethylene oxide, propylene oxide, butylene oxide, 1,2-epoxyhexane, 1,2-epoxyoctane, cyclic epoxides such as cyclohexene oxide or exo-2,3-epoxynorborane. The polyoxyalkylene group comprises predominately oxyethylene units ($C_2H_4O$), but may also contain minor amounts of oxypropylene units ($C_3H_6O$), oxybutylene units ($C_4H_8O$), or mixtures thereof. Typically, the polyoxyalkylene group comprises a majority of oxyethylene units, as defined on a molar basis and indicated in the above formula by the "a" subscript. When present, the oxypropylene units are indicated in the above formula by the "b" subscript. The unsaturated aliphatic hydrocarbon group can be an alkenyl or alkynyl group. Representative, non-limiting examples of the alkenyl groups are shown by the following structures; $H_2C$=$CH$—, $H_2C$=$CHCH_2$—, $H_2C$=$CHC(CH_3)_2$—, $H_2C$=$C(CH_3)CH_2$—, $H_2C$=$CHCH_2CH_2$—, $H_2C$=$CHCH_2CH_2CH_2$—, and $H_2C$=$CHCH_2CH_2CH_2CH_2$—. Representative, non-limiting examples of alkynyl groups are shown by the following structures; $HC$≡$C$—, $HC$≡$CCH_2$—, $HC$≡$CCH(CH_3)$—, $HC$≡$CC(CH_3)_2$—, and $HC$≡$CC(CH_3)_2CH_2$—.

Polyoxyalkylenes having an unsaturated aliphatic hydrocarbon group at one molecular terminal are known in the art, and many are commercially available.

Representative, non-limiting examples of polyoxyalkylenes having an unsaturated aliphatic hydrocarbyl at one molecular terminal include;

$H_2C$=$CHCH_2O[C_2H_4O]_aH$
$H_2C$=$CHCH_2O[C_2H_4O]_a[C_3H_6O]_bH$
$H_2C$=$CHCH_2O[C_2H_4O]_aCH_3$
$H_2C$=$CHC(CH_3)_2O[C_2H_4O]_aCH_3$
$H_2C$=$CHC(CH_3)_2O[C_2H_4O]_a[C_3H_6O]_bH$
$H_2C$=$CHCH_2O[C_2H_4O]_aC(O)CH_3$
$H_2C$=$C(CH_3)CH_2O[C_2H_4O]_aH$
$HC$≡$CCH_2O[C_2H_4O]_aH$
$HC$≡$CC(CH_3)_2O[C_2H_4O]_aH$ where a and b are as defined above.

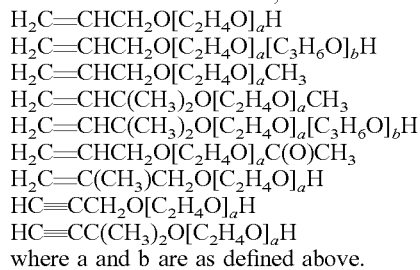

Polyoxyalkylenes having an unsaturated aliphatic hydrocarbon group at one molecular terminal are commercially available from numerous suppliers including; NOF (Nippon Oil and Fat, Tokyo, Japan), Clariant Corp. (Switzerland), and Dow Chemical Corp. (Midland, Mich.). Commercial examples of these materials include Uniox MUS-4 from NOF, Polyglykol AM 450 from Clariant, and SF 400 and SF 443 from Dow.

The amounts of components a) and b) used in the hydrosilylation reaction may vary. The molar ratio of the SiH units of component a) to the aliphatic unsaturated groups of component b) may range from 10/1 to 1/10, alternatively from 5/1 to 1/5, or alternatively from 1/1 to 1/2. Typically, the amounts of components a) and b) are selected to provide molar excess of the unsaturated groups of component b) to the SiH groups in component a).

Component c) is a hydrosilylation catalyst. The hydrosilylation catalyst may be any suitable Group VIII metal based catalyst selected from a platinum, rhodium, iridium, palladium or ruthenium. Group VIII group metal containing catalysts useful to catalyze curing of the present compositions can be any of those known to catalyze reactions of silicon bonded hydrogen atoms with silicon bonded unsaturated hydrocarbon groups. The preferred Group VIII metal for use as a catalyst to effect cure of the present compositions by hydrosilylation is a platinum based catalyst. Some preferred platinum based hydrosilylation catalysts for curing the present composition are platinum metal, platinum compounds and platinum complexes.

Suitable platinum catalysts are described in U.S. Pat. No. 2,823,218 (commonly referred to as "Speier's catalyst) and U.S. Pat. No. 3,923,705. The platinum catalyst may be "Karstedt's catalyst", which is described in Karstedt's U.S. Pat. Nos. 3,715,334 and 3,814,730. Karstedt's catalyst is a platinum divinyl tetramethyl disiloxane complex typically containing about one-weight percent of platinum in a solvent such as toluene. Alternatively the platinum catalyst may be a reaction product of chloroplatinic acid and an organosilicon compound containing terminal aliphatic unsaturation, as described in U.S. Pat. No. 3,419,593. Alternatively, the hydrosilylation catalyst is a neutralized complex of platinum chloride and divinyl tetramethyl disiloxane, as described in U.S. Pat. No. 5,175,325.

Further suitable hydrosilylation catalysts are described in, for example, U.S. Pat. Nos. 3,159,601; 3,220,972; 3,296,291; 3,516,946; 3,989,668; 4,784,879; 5,036,117; and 5,175,325 and EP 0 347 895 B1.

The hydrosilylation catalyst may be added in an amount equivalent to as little as 0.001 part by weight of elemental platinum group metal, per one million parts (ppm) of the total reaction composition. Typically, the concentration of the hydrosilylation catalyst in the reaction composition is that capable of providing the equivalent of at least 1 part per million of elemental platinum group metal. A catalyst concentration providing the equivalent of 1 to 500, alternatively 50 to 500, alternatively 50 to 200 parts per million of elemental platinum group metal may be used.

The reaction effected in the present process is a hydrosilylation reaction, wherein the SiH units of component a) react with the unsaturated aliphatic hydrocarbon group of component b) to form an Si—C bond. The reaction may be conducted under those conditions known in the art for effecting hydrosilylations reactions.

The hydrosilylation reaction can be conducted neat or in the presence of a solvent. The solvent can be an alcohol such as methanol, ethanol, isopropanol, butanol, n-propanol, or branched guerbet alcohols; a ketone such as acetone, methylethyl ketone, or methyl isobutyl ketone; an aromatic hydrocarbon such as benzene, toluene, or xylene; an aliphatic hydrocarbon such as heptane, hexane, or octane; a glycol ether such as propylene glycol methyl ether, dipropylene glycol methyl ether, propylene glycol n-butyl ether, propylene glycol n-propyl ether, or ethylene glycol n-butyl ether; a halogenated hydrocarbon such as dichloromethane, 1,1,1-trichloroethane or methylene chloride, chloroform; dimethyl sulfoxide; dimethyl formamide; acetonitrile; tetrahydrofuran; white spirits; mineral spirits; or naphtha.

The amount of solvent can be up to 70 weight percent, but is typically from 20 to 50 weight percent, said weight percent being based on the total weight of components in the hydrosilylation reaction. The solvent used during the hydrosilylation reaction can be subsequently removed from the resulting silicone polyether by various known methods.

Additional components can be added to the hydrosilylation reaction which are known to enhance such reactions. These components include salts such as sodium acetate which have a buffering effect in combination with platinum catalysts.

B) The Water Immiscible Silicone or Organic Liquid

Component B) in the silicone polyether microemulsion is optional, and when used may be either a water immiscible silicone or a water immiscible organic liquid.

Organic liquids includes those considered as oils or solvents. The organic liquids are exemplified by, but not limited to, aromatic hydrocarbons, aliphatic hydrocarbons, alcohols having more than 6 carbon atoms, branched guerbet alcohols such as ISOFOL® 12, aldehydes, ketones, amines, esters, ethers, glycols, glycol ethers, alkyl halides and aromatic halides. Hydrocarbons include isododecane, isohexadecane, Isopar L (C11-C13), Isopar H (C11-C12), hydrogenated polydecene. Ethers and esters include alkyl benzoates, isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, and octyl palmitate.

Component B may also be a polydialkylsiloxane or a volatile methyl siloxane having a viscosity at 25° C. in the range of 1 to 1,000 mm$^2$/sec such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadecamethylheptasiloxane, heptamethyl-3-{(trimethylsilyl)oxy)}trisiloxane, hexamethyl-3,3,bis{(trimethylsilyl)oxy}trisiloxane pentamethyl {(trimethylsilyl)oxy}cyclotrisiloxane as well as polydimethylsiloxanes, polyethylsiloxanes, polymethylethylsiloxanes, polymethylphenylsiloxanes, polydiphenylsiloxanes, and any mixtures thereof.

In one embodiment, component B) is present in the water immiscible dispersed phase of the microemulsion and is $C_{12}$-$C_{15}$ alkyl benzoate.

In one embodiment, component B is present in the water immiscible dispersed phase of the microemulsion and is $C_{12}$-$C_{32}$ branched guerbet alcohols.

In one embodiment, component B is present in the water immiscible dispersed phase of the microemulsion and is a linear polydimethylsiloxane, that may be silanol terminated or trimethylsiloxy terminated, having a viscosity ranging from 1 to 1,000 mm$^2$/sec, alternatively 10 to 500 mm$^2$/sec, alternatively 10 to 100 mm$^2$/sec at 25° C.

The amount of component B) in the water immiscible dispersed phase of the microemulsion may range from 0 to 50 weight percent, alternatively from 0 to 40 wt. %, alternatively from 0 to 30 wt. %, alternatively from 0 to 20 wt. %, alternatively from 0 to 10 wt. %, alternatively from 0 to 5 wt. %, of the total amount of the water immiscible dispersed phase used in the microemulsion.

C) The Emulsifier

The present microemulsions contain at least 5% by weight of an emulsifier selected from an anionic surfactant, a cationic surfactant, a nonionic surfactant, an amphoteric or a combination thereof. As used herein, "emulsifier" refers to any compound or substance that enables the formation of an emulsion. The emulsifier may be selected from any surface active compound or polymer capable of stabilizing emulsions, providing the emulsifier contains at least one anionic, cationic, amphoteric or nonionic surfactant and is used in sufficient quantities to provide the microemulsion with at least 5 weight %, alternatively 10 wt % of the anionic, cationic, amphoteric or nonionic surfactant. Typically, such surface active compounds or polymers stabilize emulsions by preventing coalescence of the dispersed particles. The surface active compounds useful as emulsifiers in the present compositions are anionic, cationic, amphoteric or nonionic surfactant or combination of surfactants. Mixtures of surfactants of different types and/or different surfactants of the same type can be used.

In one embodiment, the surfactant or combination of surfactants selected as component C) are those that are capable of forming bi-layer structures, such as lamellar phases, when dispersed in water. More specifically, the surfactant(s) may be selected from those that form lamellar structures when 20-80 weight % of the surfactant(s) are dispersed in water at room temperature or a disordered bi-layer structure when 1-20 weight % of the surfactant(s) are dispersed in water at 20-90° C. The presence of bi-layers, such as lamellar structures, may be readily determined by various techniques such as optical microscopy using cross-polarized light. Although not wishing to be bound by theory, the present inventors believe surfactant(s) capable of forming bi-layers (such as lamellar or disordered) enhances the formation of the microemulsion. In particular, the polydialkylsiloxane-polyoxyalkylene copolymer may be solubilised in or inter-penetrate with the bi-layer structure formed by the surfactants and water, and subsequently forms the microemulsion. Alternatively, the polydialkylsiloxane-polyoxyalkylene copolymer, the surfactants and water form a new assembly structure such as a spherical, spheroidal or cylindrical structure, different from the bi-layer structure that the surfactant(s) and water alone form. In either case, the final structure has a geometry such that the length scale in at least one dimension is less than 100 nanometer. It should be further understood the presence of surfactant bi-layers is not required in the final microemulsion compositions. Rather, the discovery taught in this embodiment allows one skilled in the art to more readily choose appropriate surfactant(s) as component C) to prepare the present microemulsions.

Some suitable anionic surfactants which can be used include (i) sulfonic acids and their salts, including alkyl, alkylaryl, alkylnapthalene, and alkyldiphenylether sulfonic acids, and their salts, having at least 6 carbon atoms in the alkyl substituent, such as dodecylbenzensulfonic acid, and its sodium salt or its amine salt; (ii) alkyl sulfates having at least 6 carbon atoms in the alkyl substituent, such as sodium lauryl sulfate; (iii) the sulfate esters of polyoxyethylene monoalkyl ethers; (iv) long chain carboxylic acid surfactants and their salts, such as lauric acid, steric acid, oleic acid, and their alkali metal and amine salts.

In one embodiment, the emulsifier is sodium alkyl sulfonate such as HOSTAPUR® SAS-30. In one embodiment, the emulsifier is triethanolamine dodecylbenzene sulfonate, such as BIO-SOFT N 300®

Some suitable nonionic surfactants which can be used include polyoxyethylene alkyl ethers, polyoxyethylene alkyl phenyl ethers, alkylglucosides, polyoxyethylene fatty acid esters, sorbitan fatty acid esters, and polyoxyethylene sorbitan fatty acid esters. Nonionic surfactants which are commercially available include compositions such as (i) 2,6,8-trimethyl-4-nonyl polyoxyethylene ether sold under the names Tergitol TMN-6 and Tergitol TMN-10; (ii) the C11-15 secondary alkyl polyoxyethylene ethers sold under the names Tergitol 15-S-7, Tergitol 15-S-9, Tergitol 15-5-15, Tergitol 15-S-30, and Tergitol 15-S-40, by the Dow Chemical Company, Midland, Mich.; octylphenyl polyoxyethylene (40) ether sold under the name Triton X405 by the Dow Chemical Company, Midland, Mich.; (iii) nonylphenyl polyoxyethylene (10) ether sold under the name Makon 10 by the Stepan Company, Northfield, Ill.; (iv) ethoxylated alcohols sold under the name Trycol 5953 by Henkel Corp./Emery Group, Cincinnati, Ohio; (v) ethoxylated alcohols sold under the name Brij L23 and Brij L4 by Croda Inc. Edison, N.J.; (vi) alkyl-oxo alcohol polyglycol ethers such as GENAPOL UD 050, and Genapol UD110, (vii) alkyl polyethylene glycol ether based on C10-Guerbet alcohol and ethylene oxide such as LUTENSOL® XP 79.

Suitable nonionic surfactants also include poly(oxyethylene)-poly(oxypropylene)-poly(oxyethylene) tri-block copolymers. Poly(oxyethylene)-poly(oxypropylene)-poly(oxyethylene) tri-block copolymers are also commonly known as Poloxamers. They are nonionic triblock copolymers composed of a central hydrophobic chain of polyoxypropylene (poly(propylene oxide)) flanked by two hydrophilic chains of polyoxyethylene (poly(ethylene oxide)). Poly(oxyethylene)-poly(oxypropylene)-poly(oxyethylene) tri-block copolymers are commercially available from BASF (Florham Park, N.J.) and are sold under the tradename PLURONIC®, such as Pluronic L61, L62, L64, L81, P84.

The nonionic surfactant may also be a silicone polyether (SPE), providing the SPE selected as an emulsifier does not have a structure as described above for the polydialkylsiloxane-polyoxyalkylene copolymer as component A). The silicone polyether as an emulsifier may have a rake type structure wherein the polyoxyethylene or polyoxyethylene-polyoxypropylene copolymeric units are grafted onto the siloxane backbone, or the SPE can have an ABA block copolymeric structure wherein A represents the polyether portion and B the siloxane portion of an ABA structure. Suitable silicone polyethers include DC 5329.

Some suitable cationic surfactants which can be used include (i) fatty acid amines and amides and their salts and derivatives; such as aliphatic fatty amines and their derivatives; and (ii) quaternary ammonium compounds such as alkyl trimethylammonium and dialkyldimethylammonium halides, or acetates, or hydroxides, having at least 8 carbon atoms in each alkyl substituent. Cationic surfactants that are commercially available include compositions sold under the names Arquad T27 W, Arquad 16-29, by Akzo Nobel Chemicals Inc., Chicago, Ill.; and Ammonyx Cetac-30 by the Stepan Company, Northfield, Ill.

Suitable amphoteric surfactants include betaines such as cocamidopropylbetaine, sultaines such as cocamidopropylhydroxysultaine, lecithin and hydrogenated lecithin. In one embodiment, the emulsifier is a combination of an anionic and nonionic surfactant. In a further embodiment, the anionic surfactant in the combination is an alkyl sulfonate or a dodecylbenzene sulfonate. In a further embodiment, the nonionic emulsifier is an alkyl-oxo alcohol polyglycol ether or an alkyl polyethylene glycol ether.

When a combination of anionic surfactant and nonionic surfactants is used as the emulsifier, the amounts on a weight basis may vary to provide a ratio from 0.1 to 2, alternatively from 0.1 to 0.5 of the anionic to nonionic.

In one embodiment, the emulsifier is a combination of a cationic and nonionic surfactant, for example cetyltrimethylammonium chloride and an alkyl-oxo alcohol polyglycol ether or an alkyl polyethylene glycol ether. When a combination of cationic surfactant and nonionic surfactants is used as the emulsifier, the amounts on a weight basis may vary to provide a ratio from 0.1 to 2, alternatively from 0.1 to 0.5 of the cationic to nonionic.

The aqueous silicone polyether microemulsion comprising components A), B), and C) further contains sufficient water or an aqueous phase to sum to 100 weight percent. As used herein "aqueous phase" describes any aqueous solution containing single or multiple water soluble solutes. The aqueous phase used in the present microemulsions may contain various other components, such as certain salts, biocides, freeze/thaw additives, that may enhance the microemulsion storage stability.

The present microemulsions may be prepared by combining components A), optionally component B), component C) with certain amounts of water or an aqueous phase component, and mixing. Thus, the present silicone polyether microemulsions may be prepared by mixing at least 20% by weight of;

I a polydialkylsiloxane-polyoxyalkylene copolymer having the average formula:

$$R^1{}_3SiO[R^1{}_2SiO]_x[R^1R^2SiO]_ySiR^1{}_3 \text{ or } R^1{}_2R^2SiO[R^1{}_2SiO]_xSiR^1{}_2R^2$$

wherein
x ranges from 50 to 1000,
y ranges from 1 to 50,
$R^1$ is an alkyl group containing 1 to 6 carbon atoms,
$R^2$ is a polyoxyalkylene group having the average formula:

$$-R^3O(C_2H_4O)_a(C_3H_6O)_bR^4$$

wherein
a is greater than 4,
b ranges from 0 to 30,
$R^3$ is a divalent hydrocarbon group containing 2 to 12 carbon atoms,
$R^4$ is hydrogen,
R1, or an acetyl group, with the proviso that the polydialkylsiloxane-polyoxyalkylene copolymer contains 0.1 to 10 wt % ethylene oxide ($C_2H_4O$) groups, II optionally, a water immiscible silicone or hydrocarbon fluid, and at least 5% by weight of III an emulsifier selected from an anionic surfactant, a cationic surfactant, a nonionic surfactant, or a combination thereof, and sufficient water or an aqueous phase to sum to 100% by weight.

In this method, components A), B), and C) are the same as described above for the microemulsion composition. These components can be mixed simply with water or an aqueous phase as described above.

Mixing of components A), B), and C) with the certain amounts of water or aqueous phase component can be accomplished by any method known in the art to effect the formation of an emulsion. The mixing may occur either as a batch, semi-continuous, or continuous process. Mixing may occur, for example using, batch mixing equipments with medium/low shear include change-can mixers, double-planetary mixers, conical-screw mixers, ribbon blenders, double-arm or sigma-blade mixers; batch equipments with high-shear and high-speed dispersers include those made by Charles Ross & Sons (NY), Hockmeyer Equipment Corp. (NJ); batch equipments with high shear actions include Banbury-type (CW Brabender Instruments Inc., NJ) and Henschel type (Henschel mixers America, Tex.). Illustrative examples of continuous mixers rotor-stator, ex. Ultra Turrax®/compounders include extruders single-screw, twin-screw, and multi-screw extruders, co-rotating extruders. Alternatively, mixing may also occur via those techniques known in the art to provide high shear mixing to effect formation of emulsions. Representative of such high shear mixing techniques include high speed stirrers, homogenizers, Sonolators®, microfluidizers, Ross mixers, Eppenbach colloid mills, Flacktek Speedmixers, and other similar shear devices.

The present silicone microemulsion compositions are optically transparent. As used herein, "optically transparent" means the microemulsion have an optical transmittance of visible light greater than 85%. Transmittance was measured using a Shimadzu UV-2401 PC UV-VIS Recording Spectrophotometer at 580 nm wavelength using sample cell of 1 cm×1 cm dimension. Percent transmittance is defined as transmitted light intensity per incident light. With this measurement, white emulsions typically have transmittance less than 1%.

The present silicone polyether microemulsions may be characterized by volume average particle size of the silicone polyether (oil) phase dispersed in the aqueous phase. The particle size may be determined by laser diffraction of the microemulsion. Suitable laser diffraction techniques are well known in the art, such as the NANOTRAC™ particle sizer. The particle size is obtained from a particle size distribution (PSD). The PSD can be determined on a volume, surface, length basis. The volume particle size is equal to the diameter of the sphere that has the same volume as a given particle. The term Dv represents the volume average particle size of the dispersed particles. Dv 0.5 is the particle size measured in volume corresponding to 50% of the cumulative particle population. In other words if Dv 0.5=10 μm, 50% of the particle have an volume average particle size below 10 μm and 50% of the particle have a volume average particle size above 10 μm. Unless indicated otherwise all volume average particle sizes are calculated using Dv 0.5.

The volume average particle size of the dispersed silicone polyether (or silicone polyether/water immiscible organic or silicone liquid combination) particles is less than or equal to 100 nm.

In one embodiment the microemulsion may be considered as having a "high solids" level. More specifically, in this embodiment the microemulsion comprises, alternatively consists essentially of, or alternatively consists of;
40-60 wt % of a dispersed phase of A) the polydialkylsiloxane-polyoxyalkylene copolymer, 0-20 wt % B) the water immiscible silicone or hydrocarbon fluid, and
10-40 wt % C) the emulsifier,
with sufficient water or aqueous phase to sum to 100 wt %.

Such "high solids" microemulsions are often clear gels or clear liquids having a viscosity greater than 10 Pascal·second (Pa·s), or equivalently $10^4$ centipoise at 23° C. Furthermore, they are often viscoelastic. (Viscoelastic materials are non-Newtonian, i.e., their viscosity varies with shear rate.) In the latter case, the magnitude of the complex viscosity varies in the range from 10 to $10^7$ Pascal second, or equivalently from $10^4$ to $10^{10}$ centipoise at a shear frequency of from 100 Herz to 0.001 Herz when measured in an oscillatory motion. Such "high solids" microemulsions can nonetheless be diluted in water to any arbitrary extent and still retain clarity. Sufficiently diluted microemulsions from these gel microemulsions are liquid-like and Newtonian, and when thin enough, they are water-like.

Compositions comprising the present microemulsions may be formulated into personal care product compositions. The personal care compositions of this invention may be in the form of a cream, a gel, a powder, a paste, or a freely pourable liquid. Generally, such compositions can generally be prepared at room temperature if no solid materials at room temperature are presents in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care products may be functional with respect to the portion of the body to which they are applied, cosmetic, therapeutic, or some combination thereof. Conventional examples of such products include, but are not limited to:

antiperspirants and deodorants, skin care creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, powders, medicament creams, pastes or sprays including antiacne, dental hygienic, antibiotic, healing promotive, nutritive and the like, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier is readily apparent to one of ordinary skill in the art.

The present microemulsion compositions can be used in a variety of personal, household, and healthcare applications. In particular, the compositions of the present invention may be used in the personal care products as taught in U.S. Pat. Nos. 6,051,216, 5,919,441, 5,981,680; as disclosed in WO 2004/060271 and WO 2004/060101; in sunscreen compositions as taught in WO 2004/060276; in cosmetic compositions also containing film-forming resins, as disclosed in WO 03/105801; in the cosmetic compositions as taught in US Patent Application Publications 2003/0235553, 2003/0072730, 2003/0170188, EP 1,266,647, EP 1,266,648, EP1, 266,653, WO 03/105789, WO 2004/000247 and WO 03/106614; as additional agents to those taught in WO 2004/054523; in long wearing cosmetic compositions as taught in US Patent Application Publication 2004/0180032; in transparent or translucent care and/or make up compositions as discussed in WO 2004/054524.

In yet another aspect the present emulsions can be used as part of colorant or fixative compositions and applied as pre-, during-, post-treatment in the process of colouring or perming hair. The purposes could range from color retention and color enhancement to again conditioning of the coloured hair fibres. Examples and preferred embodiments can be found in the patent documents EP1312343A2, EP1312348A2, EP1312349A2, EP1312337, EP1312650, EP1312342 A2, EP1312341 A2, WO2007071684, US20080282482 by L'Oreal and EP1543820 by Procter and Gamble, all of which are incorporated herein by reference.

The compositions according to this invention can be used by the standard methods, such as applying them to the human body, e.g. skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the compositions according to the present invention may be used in a conventional manner for example for conditioning the skin. An effective amount of the composition for the purpose is applied to the skin. Such effective amounts generally range from about 1 mg/cm$^2$ to about 3 mg/cm$^2$. Application to the skin typically includes working the composition into the skin. This method for applying to the skin comprises the steps of contacting the skin with the composition in an effective amount and then rubbing the composition into the skin. These steps can be repeated as many times as desired to achieve the desired benefit.

The use of the compositions according to the invention on hair may use a conventional manner for conditioning hair. An effective amount of the composition for conditioning hair is applied to the hair. Such effective amounts generally range from about 0.5 g to about 50 g, preferably from about 1 g to about 20 g. Application to the hair typically includes working the composition through the hair such that most or all of the hair is contacted with the composition. This method for conditioning the hair comprises the steps of applying an effective amount of the hair care composition to the hair, and then working the composition through the hair. These steps can be repeated as many times as desired to achieve the desired conditioning benefit.

Non-limiting examples of additives which may be formulated into the personal care compositions in addition to the present microemulsions include: additional silicones, anti-oxidants, cleansing agents, colorants, additional conditioning agents, deposition agents, electrolytes, emollients, oils, exfoliating agents, foam boosters, fragrances, humectants, occlusive agents, pediculicides, pH control agents, pigments, preservatives, biocides, other solvents, stabilizers, sun-screening agents, suspending agents, tanning agents, other surfactants, thickeners, vitamins, botanicals, fragrances, waxes, rheology-modifying agents, anti-dandruff, anti-acne, anti-carrie and wound healing-promotion agents.

The personal care composition, such as a shampoo or cleanser may contain at least one anionic detersive surfactant. This can be any of the well-known anionic detersive surfactants typically used in shampoo formulations. These anionic detersive surfactants function as cleansing agents and foaming agents in the shampoo compositions of this invention. The anionic detersive surfactants are exemplified by alkali metal sulforicinates, sulfonated glyceryl esters of fatty acids such as sulfonated monoglycerides of coconut oil acids, salts of sulfonated monovalent alcohol esters such as sodium oleylisethianate, amides of amino sulfonic acids such as the sodium salt of oleyl methyl tauride, sulfonated products of fatty acids nitriles such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid. Preferably the detersive surfactant is selected from the group consisting of sodium lauryl sulfate, ammonium lauryl sulfate, triethanolamine lauryl sulfate, sodium lauryl ether sulfate, and ammonium lauryl ether sulfate. The anionic detersive surfactant is present in the shampoo compositions of this invention in an amount from about 5 to 50 wt % and preferably about 5 to 25 wt % based on the total weight of the composition.

The personal care composition may contain at least one cationic deposition aid, preferably a cationic deposition polymer. The cationic deposition aid will generally be present at levels of from 0.001 to 5%, preferably from about 0.01 to 1%, more preferably from about 0.02% to about 0.5% by weight. The polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof. The cationic charge density has been found to need to be at least 0.1 meq/g, preferably above 0.8 or higher. The cationic charge density should not exceed 4 meq/g, it is preferably less than 3 and more preferably less than 2 meq/g. The charge density can be measured using the Kjeldahl method and should be within the above limits at the desired pH of use, which will in general be from about 3 to 9 and preferably between 4 and 8. The cationic nitrogen-containing group will generally be present as a substituent on a fraction of the total monomer units of the cationic deposition polymer. Thus when the polymer is not a homopolymer it can contain spacer noncationic monomer units. Such polymers are described in the CTFA Cosmetic Ingredient Directory, 3rd edition. Suitable cationic deposition aids include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol. The cationic amines can be primary, secondary or tertiary amines, depending upon the particular species and the pH of the composition. In general secondary and tertiary amines, especially tertiary, are preferred. Amine substituted vinyl monomers and amines can be polymerized in the amine form and then converted to ammonium by quaternization. Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the C1-C2 alkyls, more preferably C1 and C2 alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide. The cationic deposition aids can comprise mixtures of monomer units derived from amine- and/or quaternary ammonium-substituted monomer and/or compatible spacer monomers. Suitable cationic deposition aids include, for example: copolymers of 1-vinyl-2-pyrrolidine and 1-vinyl-3-methylimidazolium salt (e.g., Chloride salt) (referred to in the industry by the Cosmetic, Toiletry, and Fragrance Association, "CTFA". as Polyquaternium-16) such as those commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate (referred to in the industry by CTFA as Polyquaternium-11) such as those commercially from Gar Corporation (Wayne, N.J., USA) under the GAFQUAT tradename (e.g., GAFQUAT 755N); cationic diallyl quaternary ammonium-containing polymer including, for example, dimethyldiallyammonium chloride homopolymer and copolymers of acrylamide and dimethyldiallyammonium chloride, referred to in the industry (CTFA) as Polyquaternium 6 and Polyquaternium 7, respectively; mineral acid salts of aminoalkyl esters of homo- and co-polymers of unsaturated carboxylic acids having from 3 to 5 carbon atoms, as described in U.S. Pat. No. 4,009,256; and cationic polyacrylamides as described in WO95/22311. Other cationic deposition aids that can be used include polysaccharide polymers, such as cationic cellulose derivatives and cationic starch derivatives. Cationic polysaccharide polymer materials suitable for use in compositions of the invention include those of the formula: A-O(R—N$^+$R$^1$R$^2$R$^3$X$^-$) wherein: A is an anhydroglucose residual group, such as starch or cellulose anhydroglucose residual, R is an alkylene oxyalklene, polyoxyalkylene, or hydroxyalkylene group, or combination thereof, R1, R2 and R3 independently are alkyl, aryl, alkylaryl, arylalkyl, alkoxyalkyl, or alkoxyaryl groups, each group containing up to about 18 carbon atoms, and the total number of carbon atoms for each cationic moiety preferably being about 20 or less, and X is an anionic counterion, as previously described. Cationic cellulose is available from Amerchol Corp. (Edison, N.J., USA) in their Polymer IR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200. Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein).

The personal care composition may contain a foam boosting agent. A foam booster is an agent which increases the amount of foam available from a system at a constant molar concentration of surfactant, in contrast to a foam stabilizer which delays the collapse of a foam. Foam building is provided by adding to the aqueous media an effective amount of a foam boosting agent. The foam boosting agent is preferably selected from the group consisting of fatty acid alkanolamides and amine oxides. The fatty acid alkanolamides are exemplified by isostearic acid diethanolamide, lauric acid diethanolamide, capric acid diethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide. The amine oxides are exemplified by N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, bis(2-hydroxyethyl) C12-15 alkoxypropylamine oxide. Preferably a foam booster is selected from the group consisting of lauric acid diethanolamide, N-lauryl dimethylamine oxide, coconut acid diethanolamide, myristic acid diethanolamide, and oleic acid diethanolamide. The foam boosting agent is preferably present in the shampoo compositions of this invention in an amount from about 1 to 15 wt % and more preferably about 2 to 10 wt % based on the total weight of the composition. The composition may further comprise a polyalkylene glycol to improve lather performance. Concentration of the polyalkylene glycol in the shampoo composition may range from about 0.01% to about 5%, preferably from about 0.05% to about 3%, and more preferably from about 0.1% to about 2%, by weight of the composition. The optional polyalkylene glycols are characterized by the general formula: H(OCH2CHR)n-OH wherein R is selected from the group consisting of H, methyl, and mixtures thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist. In the above structure, n has an average value of from about 1500 to about 25,000, preferably from about 2500 to about 20,000, and more preferably from about 3500 to about 15,000. Polyethylene glycol polymers useful herein are PEG-2M wherein R equals H and n has an average value of about 2,000 (PEG-2M is also known as Polyox WSR9 N-10, which is available from Union Carbide and as PEG-2,000); PEG-5M wherein R equals H and n has an average value of about 5,000 (PEG-5M is also known as Polyox WSRO N-35 and Polyox WSRS N-80, both available from Union Carbide and as PEG-5,000 and Polyethylene Glycol 300,000); PEG-7M wherein R equals H and n has an average value of about 7,000 (PEG-7M is also known as Polyox WSRO N-750 available from Union Carbide); PEG-9M wherein R equals H and n has an average value of about 9,000 (PEG 9-M is also known as Polyox WSRS N-3333 available from Union Carbide); and PEG14 M wherein R equals H and n has an average value of about 14,000 (PEG-14M is also known as Polyox WSRO N-3000 available from Union Carbide). Other useful polymers include the polypropylene glycols and mixed polyethylene/polypropylene glycols.

The personal care composition may contain a suspending agent at concentrations effective for suspending the preferred silicone conditioning agent, or other water-insoluble material, in dispersed form in the shampoo compositions. Such concentrations range from about 0.1% to about 10%, preferably from about 0.3% to about 5.0%, by weight of the shampoo compositions. Suspending agents include crystalline suspending agents which can be categorized as acyl derivatives, long chain amine oxides, and mixtures thereof, concentrations of which range from about 0.1% to about 5.0%, preferably from about 0.5% to about 3.0%, by weight of the shampoo compositions. These suspending agents are described in U.S. Pat. No. 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having C8-C22 chains may be used. Other long chain acyl derivatives suitable for use as suspending agents include N,N-dihydrocarbyl amido benzoic acid and soluble salts thereof (e.g., Na, K), particularly N,N-di(hydrogenated) C16, C18 and tallow amido benzoic acid species of this family, which are commercially available from Stepan Company (Northfield, Ill., USA). Examples of suitable long chain amine oxides for use as suspending agents include alkyl (C16-C22) dimethyl amine oxides, e.g., stearyl dimethyl amine oxide. Other suitable suspending agents include xanthan gum at concentrations ranging from about 0.3% to about 3%, preferably from about 0.4% to about 1.2%, by weight of the shampoo compositions. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent in the shampoo compositions. Such combinations are described in U.S. Pat. No. 4,704,272, which description is incorporated herein by reference. Other suitable suspending agents include carboxyvinyl polymers. Preferred among these polymers are the copolymers of acrylic acid crosslinked with polyallylsucrose as described in U.S. Pat. No. 2,798,053, which description is incorporated herein by reference. Examples of these polymers include Carbopol 934, 940, 941, and 956. available from B. F. Goodrich Company. Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer. Other suitable suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, etc.

The personal care composition may contain one or more water-soluble emollients including, but not limited to, lower molecular weight aliphatic diols such as propylene glycol and butylene glycol; polyols such as glycerine and sorbitol; and polyoxyethylene polymers such as polyethylene glycol 200. The specific type and amount of water soluble emollient(s) employed will vary depending on the desired aesthetic characteristics of the composition, and is readily determined by one skilled in the art.

The personal care composition may contain various oils. The term "oil" as used herein refers to any material which is substantially insoluble in water. When the composition is to be used in a cosmetic or personal care product, the product components must also be cosmetically acceptable or otherwise meet the conditions of the end use product. Suitable oil components include, but are not limited to, natural oils such as coconut oil; hydrocarbons such as mineral oil and hydrogenated polyisobutene; fatty alcohols such as octyldodecanol; esters such as C12-C15 alkyl benzoate; diesters such as propylene dipelarganate; and triesters, such as glyceryl trioctanoate and silicones especially cyclomethicone and dimethicone and mixtures thereof. The composition of the invention also contains oils, preferably a mixture of low viscosity and high viscosity oils. Suitable low viscosity oils have a viscosity of 5 to 100 mPa·s at 25° C., and are generally esters having the structure RCO—OR' wherein RCO represents the carboxylic acid radical and wherein OR is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or mixtures of octyldodecanol, acetylated lanolin alcohol, cetyl acetate, isododecanol, polyglyceryl-3-diisostearate, or mixtures thereof. The high viscosity surface oils generally have a viscosity of 200-1,000,000 mPa·s at 25° C., preferably a viscosity of 100,000-250,000 mPa·s. Surface oils include castor oil, lanolin and lanolin derivatives, triisocetyl citrate, sorbitan sesquioleate, C10-18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or mixtures thereof. The suggested ratio of low viscosity to high viscosity oils in the oil phase is 1:15 to 15:1, preferably 1:10 to 10:1 respectively. The preferred formulation of the invention comprises 1 to 20% of a mixture of low viscosity and high viscosity surface oils. Mention may be made, among the optional other non-silicone fatty substances, of mineral oils, such as liquid paraffin or liquid petroleum, of animal oils, such as perhydrosqualene or arara oil, or alternatively of vegetable oils, such as sweet almond, calophyllum, palm, castor, avocado, jojoba, olive or cereal germ oil. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The personal care composition may contain various waxes. The waxes or wax-like materials generally have a melting point range of 35 to 120° C. at atmospheric pressure. Waxes in this category include synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or mixtures thereof. The preferred formulation of the invention comprises about 10-30% of a mixture of waxes. Mention may be made, among the waxes capable of being used as non-silicone fatty substances, of animal waxes, such as beeswax; vegetable waxes, such as carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis. Mention may be made, among the silicone waxes, of polymethylsiloxane alkyls, alkoxys and/or esters.

Thickening agent may be added to provide a convenient viscosity. For example, viscosities within the range of 500 to 25,000 mm$^2$/s at 25° C. or more alternatively in the range of 3,000 to 7,000 mm$^2$/s are usually suitable. Suitable thickening agents are exemplified by sodium alginate, gum arabic, polyoxyethylene, guar gum, hydroxypropyl guar gum, ethoxylated alcohols, such as laureth-4 or polyethylene glycol 400, cellulose derivatives exemplified by methylcellulose, methylhydroxypropylcellulose, hydroxypropylcellulose, polypropylhydroxyethylcellulose, starch, and starch derivatives exemplified by hydroxyethylamylose and starch amylose, locust bean gum, electrolytes exemplified by sodium chloride and ammonium chloride, and saccharides such as fructose and glucose, and derivatives of saccharides such as PEG-120 methyl glucose diolate or mixtures of 2 or more of these. Alternatively the thickening agent is selected from cellulose derivatives, saccharide derivatives, and electrolytes, or from a combination of two or more of the above thickening agents exemplified by a combination of a cellulose derivative and any electrolyte, and a starch derivative and any electrolyte. The thickening agent, where used is present in the shampoo compositions of this invention in an amount sufficient to provide a viscosity in the final shampoo present in an amount from about 0.05 to 10 wt % and alternatively 0.05 to 5 wt % based on the total weight of the composition.

Stabilizing agents can be used in the water phase of the compositions. Suitable water phase stabilizing agents can include alone or in combination one or more electrolytes, polyols, alcohols such as ethyl alcohol, and hydrocolloids. Typical electrolytes are alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate. When the stabilizing agent is, or includes, an electrolyte, it amounts to about 0.1 to 5 wt % and more alternatively 0.5 to 3 wt % of the total composition. The hydrocolloids include gums, such as Xantham gum or Veegum and thickening agents, such as carboxymethyl cellulose. Polyols, such as glycerine, glycols, and sorbitols can also be used. Alternative polyols are glycerine, propylene glycol, sorbitol and butylene glycol. If a large amount of a polyol is used, one need not add the electrolyte. However, it is typical to use a combination of an electrolyte, a polyol and an hydrocolloid to stabilize the water phase, e.g. magnesium sulfate, butylene glycol and Xantham gum.

The personal care compositions can also be under the form of aerosols in combination with propellant gases, such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether.

Silicone compositions other than the present silicone polyether microemulsions, may also be included in the personal care compositions. For example, such silicones include; silicone fluids, aminofunctional silicones, gums, resins, elastomers, and other silicone emulsions.

Amino functional silicones may be included in the present compositions. For example, the amino functional silicones may have the general formula:

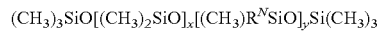

$(CH_3)_3SiO[(CH_3)_2SiO]_x[(CH_3)R^NSiO]_ySi(CH_3)_3$ where $R^N$ is an aminofunctional group.

Alkylmethylsiloxanes may be included in the present compositions. These siloxane polymers generally will have the formula $Me_3SiO[Me_2SiO]_y[MeRSiO]_zSiMe_3$, in which R is a hydrocarbon group containing 6-30 carbon atoms, Me represents methyl, and the degree of polymerization (DP), i.e., the sum of y and z is 3-50. Both the volatile and liquid species of alkymethysiloxanes can be used in the composition.

Silicone gums may be included in the present compositions. Polydiorganosiloxane gums are known in the art and are available commercially. They consist of generally insoluble polydiorganosiloxanes having a viscosity in excess of 1,000,000 centistoke (mm$^2$/s) at 25° C., alternatively greater than 5,000,000 centistoke (mm$^2$/s) at 25° C. These silicone gums are typically sold as compositions already dispersed in a suitable solvent to facilitate their handling. Ultra-high viscosity silicones can also be included as optional ingredients. These ultra-high viscosity silicones typically have a kinematic viscosity greater than 5 million centistoke (mm$^2$/s) at 25° C., to about 20 million centistoke (mm$^2$/s) at 25° C. Compositions of this type in the form of suspensions are most preferred, and are described for example in U.S. Pat. No. 6,013,682 (Jan. 11, 2000).

Silicone resins may be included in the present compositions. These resin compositions are generally highly crosslinked polymeric siloxanes. Crosslinking is obtained by incorporating trifunctional and/or tetrafunctional silanes with the monofunctional silane and/or difunctional silane monomers used during manufacture. The degree of crosslinking required to obtain a suitable silicone resin will vary according to the specifics of the silane monomer units incorporated during manufacture of the silicone resin. In general, any silicone having a sufficient level of trifunctional and tetrafunctional siloxane monomer units, and hence possessing sufficient levels of crosslinking to dry down to a rigid or a hard film can be considered to be suitable for use as the silicone resin. Commercially available silicone resins suitable for applications herein are generally supplied in an unhardened form in low viscosity volatile or nonvolatile silicone fluids. The silicone resins should be incorporated into compositions of the invention in their non-hardened forms rather than as hardened resinous structures.

Silicone carbinol fluids may be included in the present compositions. These materials are described in WO 03/101412 A2, and can be commonly described as substituted hydrocarbyl functional siloxane fluids or resins.

EXAMPLES

The following examples are included to demonstrate the invention to those of skill in the art. However, those of skill in the art should, in light of the present disclosure, appreciate that many changes can be made in the specific embodiments which are disclosed and still obtain a like or similar result without departing from the spirit and scope of the invention. All percentages are in wt. %. All measurements were conducted at 23° C. unless indicated otherwise.

Materials

Silicone Polyethers (Component A)

A series of silicone polyethers were prepared according to the following general procedure.

A polydimethylsiloxane (1181.37 g) with the following structure, $MD_{396}D^{(H)}{}_4M$, was placed in a 2000 ml three neck round bottom flask equipped with stir rod, temperature probe, heating mantle, condenser, and nitrogen purge. In addition an allyl $EO_7$ polyether (77.95 g) with the structure $CH_2=CHCH_2(OCH_2CH_2)_7OH$, and 2-butyloctanol (66.26 g), were added to the same reaction flask. To the flask also can be added 6.0 g of anhydrous sodium acetate (salt). The contents of the flask was heated to 80° C. and 0.65 g of a 1% solution of 1,3-diethenyl-1,1,3,3-tetramethldisiloxane complexed with platinum in isopropanol was added by syringe to the reaction flask. After the exotherm the reaction mixture was mixed at 80° C. for two to four hours or until the Si—H ppm was below 7.

The other silicone polyethers were prepared using a similar procedure in which all reactions were conducted using similar weight percent of the components, while maintaining a 10% excess of vinyl to SiH in the reaction.

The following silicone polyethers were prepared, according to the general procedures described above, having the general formula $Me_3SiO[Me_2SiO]_x[MeR^2SiO]_ySiMe_3$ where $R^2$ is $—CH_2CH_2CH_2(C_2H_4O)_a(C_3H_6O)_bOH$. The values for x, y, a, and b are summarized below;

Silicone Polyether
I x=544 y=5.9 a=10 b=4
II x=396 y=4 a=10 b=4
III x=370 y=7 a=10 b=4
IV x=400 y=4 a=7 b=0 salt used in hydrosilation
V x=400 y=4 a=7 b=0 no salt used in hydrosilation
VI x=400 y=4 a=12 b=0 no salt used in hydrosilation
VII x=400 y=8 a=7 b=0 salt used in hydrosilation
VIII x=200 y=4 a=10 b=4
IX ABA type (with same $R^2$ group, but on endcapping group) with x=100 y=0 a=7 salt used in hydrosilation The following organic or silicone fluids were used as optional component B) in the below examples Optional Fluid
a Isofol-12
b C12-15 Alkyl Benzoate
c Dow Corning® Q1-3563 Fluid
d Dow Corning® 200 Fluid 50 cSt The following emulsifiers were used as component C).
Emulsifier
i HOSTAPUR SAS-30 (30% active emulsifier in water)
ii Lutensol XP-79 (85% active emulsifier in water)
iii Genapol UD-050 (100% active)
iv Bio-Soft N300 (60% active emulsifier in water)
v Bio-Soft EC 690 (90% active in water)
vi T Max 20

Example 1

Preparation of Silicone Polyether Microemulsions

A series of silicone polyether microemulsions were prepared, as summarized in Table 1 using the following general procedure.

In a suitable container of the SpeedMixer™ (model DAC 150 FVZ) was mixed the polydiorganosiloxane-polyoxyalkylene copolymer and any optional silicone or hydrocarbon fluid. To the content was then added the emulsifier(s) and an appropriate amount of water. The content was mixed in a SpeedMixer™ at 3500RPM for 30 seconds to arrive at a clear or translucent microemulsion. The microemulsion can be further diluted with water. Particle size was measured by a Nanotrac™ particle sizer in volume mode. Quantitative details are listed in Table 1.

TABLE 1

| Sample Reference | Silicone Polyether | Optional Silicone Or Organic Fluid | Emulsifier 1 | Emulsifier 2 | Water | Additional Dilution Water | Appearance | Median Particle Size (nanometer) |
|---|---|---|---|---|---|---|---|---|
| A | $30^I$ | | $6.0^i$ | $10.5^{ii}$ | 10.5 | 43.0 | clear | 18.8 |
| B | $30^I$ | $1.5^a$ | $8.0^i$ | $9.0^{ii}$ | 10.0 | 41.5 | clear | 15.0 |
| C | $30^I$ | $3.0^b$ | $6.0^i$ | $10.5^{ii}$ | 10.5 | 40.0 | clear | 16.4 |
| D | $30^{II}$ | | $6.0^i$ | $10.5^{ii}$ | 7.5 | 46 | clear | 24.5 |
| E | $30^{II}$ | $1.5^a$ | $8.0^i$ | $9.0^{ii}$ | 7.0 | 44.5 | clear | 21.2 |
| F | $30^{III}$ | | $6.0^i$ | $8.95^{iii}$ | 10.5 | 44.5 | clear | 8.4 |
| G | $30^{III}$ | $1.5^a$ | $8.0^i$ | $7.65^{iii}$ | 10.0 | 42.8 | clear | 8.3 |
| H | $25^{IV}$ | | $5.0^i$ | $11.0^{ii}$ | 6.3 | 36.0 | clear | 24.8 |
| I | $25^V$ | | $5.0^i$ | $11.0^{ii}$ | 6.4 | 36.1 | clear | 20.1 |
| J | $25^{VI}$ | | $5.0^i$ | $11.0^{ii}$ | 7.5 | 34.8 | clear | 20.7 |
| K | $25^{VII}$ | | $5.0^i$ | $10.0^{ii}$ | 20.0 | 23.4 | translucent | 14.6 |
| L | $25^{VIII}$ | | $5.0^i$ | $10.0^{ii}$ | 20.0 | 23.2 | clear | 7.1 |
| M | $26^{VIII}$ | | $5.0^i$ | $8.8^{ii}$ | 5.0 | 39.5 | translucent | 26.7 |
| N | $30^{II}$ | | $8.0^i$ | $10.0^{ii}$ | 8.0 | 42.0 | translucent | 27.8 |
| O | $33.5^{IV}$ | | $6.9^i$ | $13.9^{ii}$ | 8.7 | 37.0 | clear | |
| P | $22.9^{IV}$ | $12.4^c$ | $3.5^{ix}$ | $14.1^{ii}$ | 11.8 | 35.3 | clear | |
| Q | $20^{IV}$ | $10.0^c$ | $3.0^{iii}$ | $9.0^{ii}$ | 7 | 51.0 | clear | |
| R | $20^{IV}$ | $10.0^d$ | $3.0^{iii}$ | $9.0^{ii}$ | 7 | 51.0 | slightly hazy | 46 |
| S | $25^{IV}$ | | $3.0^{iii}$ | $9.0^{ii}$ | 7 | 56.0 | clear | |
| T | $30^{IX}$ | | $3.0^{iii}$ | $9.0^{ii}$ | 7 | 51.0 | clear | |
| U | $20^V$ | $5.0^a$ | $12^v$ | $3^{vi}$ | 10.0 | 45.0 | clear | |
| V | $30^V$ | $2.0^a$ | $9^{ii}$ | $3^{iii}$ | 7.5 | 50.5 | clear | |

Example 2

Comparative Examples

A series of emulsions were prepared following a similar procedure as described above in Example 1. In these examples, microemulsion prepared with silicone polyether II is listed as Example 2. See Table 2. Attempts at preparing similar emulsions using a silicone polyether having the formula $Me_3SiO[Me_2SiO]_x[MeR^2SiO]_ySiMe_3$ where $R^2=—CH_2CH_2CH_2(C_3H_6O)_{2.5}OH$ (abbreviated as MD67D'3 (P02.5)M) are listed as comparative examples 2A-2F. Particle size was measured by a Nanotrac™ particle sizer in volume mode. Transmittance was measured on a Shimadzu UV/VIS 2401PC spectrometer at 580 nm wavelength using a liquid sample cell of 1 cm² square cross section. Transmittance was reported as percentage of transmitted light intensity per incident light. A visually clear or translucent emulsion typically corresponds to a transmittance of greater than 85%.

including emulsion particle size and clarity (as measured by transmittance) are to be compared with those of the microemulsion in Example 2, which demonstrates properties of the present invention. The present microemulsions also include a higher active content and a lower level of surfactant usage per active content.

TABLE 2

|  | Example |||||||
|---|---|---|---|---|---|---|---|
|  | 2 | 2A | 2B | 2C | 2D | 2E | 2F |
| Oil Phase | | | | | | | |
| MD396D(EO7)4M containing 5% isofol-12 (SPE II) | 3.00 | | | | | | |
| MD67D'3(PO2.5)M OH term PDMS 65 cst | | 10.00 | 10.00 | 3.00 | 2.04 | 10.00 | 10.00 |
| Emulsifiers | | | | | | | |
| Polyethylene(7)bis(trimethylsiloxy)methylsilyl propyl ether | | 4.30 | 4.30 | | 0.96 | 4.00 | 4.00 |
| Biosoft EC 690 | 1.20 | | | 1.20 | 1.20 | | |
| T-Maz 20 | 0.30 | | | 0.30 | 0.30 | | |
| Water | | | | | | | |
| H2O #1 | 1.00 | 1.00 | 1.00 | 1.00 | 1.00 | 2.00 | 2.00 |
| Dilution water | 1.00 | 179.90 | 17.99 | 1.00 | 1.00 | 150.00 | 15.00 |
| Dilution water | 1.00 | | | 1.00 | 1.00 | | |
| Dilution water | 1.00 | | | 2.50 | 2.50 | | |
| Dilution water | 1.50 | | | | | | |
| Additional surfactant (Triton X405) | | 4.80 | 0.48 | | | 8.00 | 0.80 |
| Total Weight (g) | 10.00 | 200.00 | 33.77 | 10.00 | 10.00 | 166.00 | 31.00 |
| Appearance-final emulsion | clear | white | white | white | white | white | white |
| Transmittance | 86% | ~0% | ~0% | ~0% | ~0% | 0.12% | ~0% |
| Dv(0.5) nm | 24.5 | 16000.0 | 685.0 | 340 | 136 | 72 | 141 |
| Dv(0.9) nm | 35.0 | 35000.0 | 5000.0 | 570 | 217 | 252 | 269 |
| Oil phase content | 30% | 5% | 30% | 30% | 30% | 6% | 32% |
| Surfactant/oil phase | 46% | 91% | 48% | 46% | 46% | 120% | 48% |

Comparative Example 2A is a repeat of example 18 in U.S. Pat. No. 4,620,878. The characteristic properties including emulsion particle size and clarity (as measured by transmittance) are to be compared with those of the microemulsion in Example 2. The present microemulsions also include a higher oil phase content (active content) and a lower level of surfactant usage per active content.

Comparative Example 2B cuts down the amount of dilutional aqueous solution containing the Triton surfactant in example 18 of 878' in order to arrive at a final emulsion with comparable active content and surfactant level as in Example 2. The measured particle size and transmittance are to be compared with those from the present Example 2.

Comparative Example 2C is to compare with example 18 in U.S. Pat. No. 4,620,878. In this comparative example, the oil phase is the polyorganosiloxane used in 878' the surfactants are as in Example 2.

Comparative Example 2D is also to compare with example 18 in 878'. In this comparative example, the oil phase is the polyorganosiloxane used in 878', the surfactants consist of the silicone glycol surfactant used in 878' but in place of the Triton X405 in 878', the surfactants used in Example 2 as the rest of the surfactant package.

Comparative Example 2E is a repeat of example 19 in U.S. Pat. No. 4,620,878. The characteristic properties Comparative Example 2F cuts down the amount of dilutional aqueous solution containing the Triton surfactant in example 19 of 878' order to arrive at a final emulsion with comparable active content and surfactant level as in Example 2. The measured particle size and transmittance are to be compared with those from the present Example 2.

Example 3 and 4

The procedure of Example 1 was repeated with no or little dilution water so as to arrive at clear microemulsions having higher oil phase (active) contents—see Table 3.

TABLE 3

| Example | 3 | 4 |
|---|---|---|
| MD396D(EO7)4M containing 5% isofol-12 (SPE II) | 55 | 40 |
| Biosoft EC 690 | 22 | 16 |
| Tmaz-20 | 5 | 4 |
| H2O #1 | 18 | 18 |
| Dilution water | | 22 |
| Total (wt %) | 100 | 100 |
| Appearance-final emulsion | clear gel | clear gel |

TABLE 3-continued

| Example | 3 | 4 |
|---|---|---|
| Oil phase (active) content | 55% | 40% |
| Surfactant/active content | 45.1% | 46.0% |

Example 5

Conditioning Shampoo

TABLE 4

| | | % Active Si | | | | | | | |
|---|---|---|---|---|---|---|---|---|---|
| | | 2 | 2 | 2 | 2 | 2 | 2 | 2 | 2 |
| | | | | | Sample - see Table 1 | | | | |
| | Ingredients | A wt % | B wt % | C wt % | D wt % | E wt % | F wt % | G wt % | XIAMETER® MEM-1870 Emulsion wt % |
| Phase A | Polyquaternium-10[1] | 0.3% | 0.3% | 0.3% | 0.3% | 0.3% | 0.3% | 0.3% | 0.3% |
| | Sodium Lauryl Ether Sulfate[2] | 30.0% | 30.0% | 30.0% | 30.0% | 30.0% | 30.0% | 30.0% | 30.0% |
| | PEG-150 Pentaerythrityl Tetrastearate[3] | 1.0% | 1.0% | 1.0% | 1.0% | 1.0% | 1.0% | 1.0% | 1.0% |
| | Deionized Water | 51.6% | 51.6% | 51.6% | 51.6% | 51.6% | 51.6% | 50.3% | 50.3% |
| Phase B | Cocamide DEA[4] | 3.0% | 3.0% | 3.0% | 3.0% | 3.0% | 3.0% | 3.0% | 3.0% |
| | Cocamidopropyl Betaine[5] | 7.0% | 7.0% | 7.0% | 7.0% | 7.0% | 7.0% | 7.0% | 7.0% |
| Phase C | Silicone Microemulsion[6] | 6.7% | 6.7% | 6.7% | 6.7% | 6.7% | 6.7% | 8.0% | 8.0% |
| Phase D | Deionized Water | q.s. | q.s. | q.s. | q.s. | q.s. | q.s. | q.s. | q.s. |
| | DMDM Hydantoin[7] | 0.4% | 0.4% | 0.4% | 0.4% | 0.4% | 0.4% | 0.4% | 0.4% |

[1]UCARE Polymer JR-30M available from Dow Chemical
[2]Standapol ES-3 ® available from Cognis Corp.
[3]Crothix ® available from Croda Inc.
[4]Monamid 705 ® available from Croda Inc.
[5]Monateric CAB-LC ® available from Croda Inc.
[6]Silicone Emulsion, 2% active silicone level
[7]Glydant ® available from Lonza, Inc.

Deionized water is added to the mixing vessel. In order to keep the active silicone loading constant throughout testing, it is necessary to adjust the water level added depending on the percent active silicone in the various emulsions used. With moderate agitation, the polyquaternium-10 is dispersed until fully dissolved and sodium lauryl ether sulfate added. This is then heated to 75° C. and the PEG-150 pentaerythrityl tetrastearate is added with continual mixing. Heat is decreased to 40° C. and cocamide DEA and cocamidopropyl betaine are added. When completely incorporated, silicone microemulsion is added to the base shampoo. The shampoo is mixed for 5-10 minutes and then DMDM hydantoin is added. The water loss is compensated for and the formulation is mixed for an additional 5 minutes. The final pH of the shampoo formulations are approximately 5.5-6.0.

The viscosity of each shampoo was measured using a Helipath viscometer (spindle 93 at 50 rpm) and the results show less of an impact on viscosity for the shampoos containing the silicone polyether functional microemulsions. The transparency of each shampoo formulation was noted by visual observation and the results showed similar to improved transparency with the shampoos containing the silicone polyether functional microemulsions. See Table 5.

TABLE 5

| Sample | Viscosity (cP) | Transparency |
|---|---|---|
| A | 5660 | almost clear |
| B | 7290 | clear |

TABLE 5-continued

| Sample | Viscosity (cP) | Transparency |
|---|---|---|
| C | 4540 | clear |
| D | 5390 | almost clear |
| E | 8530 | clear |
| F | 1628 | clear |
| G | 2720 | clear |
| 1870 Emulsion | 1760 | almost clear |

Slightly bleached European human hair from DeMeo Brothers was used for testing the conditioners prepared herein. Each tress weighed about 2.0 grams. Each tress was rinsed for 15 seconds under a stream of 40° C. tap water. Using a pipette, 1.0 gram of a solution containing nine percent of sodium lauryl sulfate was applied and lathered through the tress for 30 seconds. The tress was rinsed for 30 seconds under running water. Excess water was removed from the tress by passing the tress between the index and middle fingers of the hand. The tresses were placed on a tray covered with paper towels and dried overnight. Each tress was hand combed three times with the narrow teeth of an ACE® comb, and evaluated using INSTRON WET and INSTRON DRY COMBING procedures.

INSTRON procedures are standard, recognized, and industrially acceptable protocols, see for example, U.S. Pat. No. 5,389,364 (Feb. 14, 1995), U.S. Pat. No. 5,409,695 (Apr. 25, 1995), U.S. Pat. No. 5,419,627 (May 30, 1995), and U.S. Pat. No. 5,504,149 (Apr. 2, 1996).

For tests involving shampoos, hair tresses are rinsed with tap water for 30 seconds at 40° C. The test conditioner is applied to the tress in the amount of 0.8 gram, and the tress is stroked for 30 seconds. The tress is rinsed for 30 seconds under tap water at 40° C. Excess water is removed by pulling the tress through the index and middle fingers of the hand. The tresses are allowed to dry separately on a paper towel overnight at room temperature. The tresses are combed once before performing an INSTRON study.

INSTRON COMBING is an industry recognized test for determining hair conditioning by the ease of wet combing and the ease of dry combing. The test employs an INSTRON strain gauge, which is equipped to measure the force required to comb the hair. The conditioning performance is based on the ability of a particular hair treatment formulation, such as a shampoo or a hair conditioner, to reduce the force required to comb the hair with the INSTRON strain gauge. The force is reported as an Average Combing Load (ACL). The lower the number of the ACL value, the better is the conditioning effect imparted by the formulation being tested. Typically, ACL baselines are initially established using untreated tresses that have only been washed with a sodium lauryl sulfate solution. The effectiveness of a treatment can then be expressed as an ACL of the treated tress or percent reduction in ACL, calculated using the relationship:

(untreated hair ACL-treated hair ACL)×100 divided by the untreated hair ACL

According to the INSTRON WET COMBING method, hair is first wetted by dipping it into distilled water, and then the hair is detangled by combing the tress three times. The tress is then retangled by dipping in distilled water three times. Excess water is removed by passing the tress through the index and middle fingers of the hand twice. The tress is placed on a hanger and INSTRON combed. Retangling and INSTRON combing are repeated until all data points are collected. An average combing force of three tresses is measured for each treatment.

According to the INSTRON DRY COMBING method, hair is detangled by combing the tress 3 times. Then hair is retangled by swirling the tress clockwise 3 times and swirling it counter clockwise 3 times. The tress is then placed on a hanger and INSTRON combed. Retangle and Instron combing are repeated until all data points are collected. An average combing force for three tresses is measured for each treatment.

The results of INSTRON WET COMBING using shampoos from Table 4 are shown in Table 6. The results show that all of the silicone polyether functional microemulsion containing shampoos of the present invention provided a reduction in wet combing force. The shampoos containing the silicone polyether functional microemulsion emulsions were similar in performance to the XIAMETER® MEM-1870 Emulsion containing shampoo. The shampoos containing the silicone polyether functional containing microemulsions of the present invention are therefore capable of significantly improving the wet conditioning properties of hair.

The results of INSTRON DRY COMBING using shampoos from Table 4 are shown in Table 6. The results show that all of the silicone polyether functional microemulsion containing shampoos of the present invention provided a reduction in dry combing force. The shampoos containing the silicone polyether functional microemulsion emulsions were similar in performance to XIAMETER® MEM-1870 Emulsion containing shampoo. The shampoos containing the silicone polyether functional containing microemulsions of the present invention are therefore capable of significantly improving the dry conditioning properties of hair.

TABLE 6

| Sample | % Wet Reduction | % Dry Reduction |
|---|---|---|
| A | 58.6 | 53.1 |
| B | 64.2 | 71.5 |
| C | 67.9 | 66.0 |
| D | 73.0 | 69.4 |
| E | 73.5 | 73.7 |
| F | 69.7 | 53.2 |
| G | 69.5 | 52.2 |
| 1870 Emulsion | 80.2 | 61.0 |

TABLE 7

| | | | % Active Si | | | | | | |
|---|---|---|---|---|---|---|---|---|---|
| | | 2 | 2 | 2 | 2 | 2 | 2 | 2 | 2 |
| | | | | | Sample | | | | |
| | | H | I | J | K | L | M | N | XIAMETER® MEM-1870 Emulsion |
| | | | | | Polymer % Active | | | | |
| | Ingredients | 30 wt % | 30 wt % | 30 wt % | 30 wt % | 30 wt % | 30 wt % | 30 wt % | 25 wt % |
| Phase A | Polyquaternium-10[1] | 0.3% | 0.3% | 0.3% | 0.3% | 0.3% | 0.3% | 0.3% | 0.3% |
| | Sodium Lauryl Ether Sulfate[2] | 30.0% | 30.0% | 30.0% | 30.0% | 30.0% | 30.0% | 30.0% | 30.0% |

TABLE 7-continued

| | | % Active Si | | | | | | | |
|---|---|---|---|---|---|---|---|---|---|
| | | 2 | 2 | 2 | 2 | 2 | 2 | 2 | 2 |
| | | | | | Sample | | | | |
| | | H | I | J | K | L | M | N | XIAMETER® MEM-1870 Emulsion |
| | | | | | Polymer % Active | | | | |
| | Ingredients | 30 wt % | 30 wt % | 30 wt % | 30 wt % | 30 wt % | 30 wt % | 30 wt % | 25 wt % |
| | PEG-150 Pentaerythrityl Tetrastearate[3] | 1.0% | 1.0% | 1.0% | 1.0% | 1.0% | 1.0% | 1.0% | 1.0% |
| | Deionized Water | 51.6% | 51.6% | 51.6% | 51.6% | 51.6% | 51.6% | 51.6% | 50.3% |
| Phase B | Cocamide DEA[4] | 3.0% | 3.0% | 3.0% | 3.0% | 3.0% | 3.0% | 3.0% | 3.0% |
| | Cocamidopropyl Betaine[5] | 7.0% | 7.0% | 7.0% | 7.0% | 7.0% | 7.0% | 7.0% | 7.0% |
| Phase C | Silicone Emulsion[16] | 6.7% | 6.7% | 6.7% | 6.7% | 6.7% | 6.7% | 6.7% | 8.0% |
| Phase D | Deionized Water | q.s. | q.s. | q.s. | q.s. | q.s. | q.s. | q.s. | q.s. |
| | DMDM Hydantoin[7] | 0.4% | 0.4% | 0.4% | 0.4% | 0.4% | 0.4% | 0.4% | 0.4% |

[1]UCARE Polymer JR-30M available from Dow Chemical
[2]Standapol ES-3 ® available from Cognis Corp.
[3]Crothix ® available from Croda Inc.
[4]Monamid 705 ® available from Croda Inc.
[5]Monateric CAB-LC ® available from Croda Inc.
[6]Silicone Emulsion, 2% active silicone level
[7]Glydant ® available from Lonza, Inc.

Deionized water is added to the mixing vessel. In order to keep the active silicone loading constant throughout testing, it is necessary to adjust the water level added depending on the percent active silicone in the various emulsions used. With moderate agitation, the polyquaternium-10 is dispersed until fully dissolved and sodium lauryl ether sulfate added. This is then heated to 75° C. and the PEG-150 pentaerythrityl tetrastearate is added with continual mixing. Heat is decreased to 40° C. and cocamide DEA and cocamidopropyl betaine are added. When completely incorporated, silicone microemulsion is added to the base shampoo. The shampoo is mixed for 5-10 minutes and then DMDM hydantoin is added. The water loss is compensated for and the formulation is mixed for an additional 5 minutes. The final pH of the shampoo formulations are approximately 5.5-6.0.

The viscosity of each shampoo was measured using a Helipath viscometer (spindle 93 at 50 rpm) and the results show less of an impact on viscosity for the shampoos containing the silicone polyether functional microemulsions. The transparency of each shampoo formulation was noted by visual observation and the results showed similar to improved transparency with the shampoos containing the silicone polyether functional microemulsions. See Table 8.

TABLE 8

| Sample | Viscosity (cP) | Transparency |
|---|---|---|
| H | 11220 | almost clear |
| I | 12940 | almost clear |
| J | 19170 | almost clear |
| K | 2220 | opaque |
| L | 4030 | clear |
| M | 7300 | opaque |
| N | 14460 | opaque |
| 1870 Emulsion | 8780 | almost clear |

The results of INSTRON WET COMBING using shampoos from Table 7 are shown in Table 9. The results show that all of the silicone polyether functional microemulsion containing shampoos of the present invention provided a reduction in wet combing force. The shampoos containing the silicone polyether functional microemulsion emulsions were similar in performance to the XIAMETER® MEM-1870 Emulsion containing shampoo. The shampoos containing the silicone polyether functional containing microemulsions of the present invention are therefore capable of significantly improving the wet conditioning properties of hair.

The results of INSTRON DRY COMBING using shampoos from Table 7 are shown in Table 9. The results show that all of the silicone polyether functional microemulsion containing shampoos of the present invention provided a reduction in dry combing force. The shampoos containing the silicone polyether functional microemulsion emulsions were similar in performance to the XIAMETER® MEM-1870 Emulsion containing shampoo. The shampoos containing the silicone polyether functional containing microemulsions of the present invention are therefore capable of significantly improving the dry conditioning properties of hair.

TABLE 9

| Sample | % Wet Reduction | % Dry Reduction |
|---|---|---|
| H | 89.4 | 72.1 |
| I | 86.9 | 73.8 |
| J | 76.7 | 64.7 |
| K | 81.8 | 78.7 |
| L | 70.3 | 57.1 |
| M | 70.2 | 63.6 |

TABLE 9-continued

| Sample | % Wet Reduction | % Dry Reduction |
|---|---|---|
| N | 69.5 | 67.2 |
| 1870 Emulsion | 80.5 | 69.9 |

Wet feel/slipperiness, of the tresses treated with the shampoos containing the silicone polyether functional microemulsions, including smoothness and slipperiness, were similar or better than the tresses treated with the dimethyl silicone microemulsion containing shampoo. Dry feel/slipperiness and smoothness, of the tresses treated with the shampoos containing the silicone polyether functional microemulsions, including smoothness and slipperiness, were similar or better than the tresses treated with the dimethyl silicone microemulsion shampoo. The tresses treated with the shampoos containing the silicone polyether functional microemulsions also had similar shine and volume to the tresses treated with the dimethyl silicone microemulsion shampoo.

TABLE 10

| | | | % Active Si | |
|---|---|---|---|---|
| | | 2 | 2 | 2 |
| | | | Sample | |
| | | U | V | XIAMETER® MEM-1872 Emulsion |
| | | | Polymer % Active | |
| | Ingredients | 30 wt % | 35 wt % | 20 wt % |
| Phase A | Polyquaternium-10[1] | 0.3% | 0.3% | 0.3% |
| Phase B | Sodium Lauryl Ether Sulfate[2] | 30.0% | 30.0% | 30.0% |
| | PEG-150 Pentaerythrityl Tetrastearate[3] | 1.0% | 1.0% | 1.0% |
| | Deionized Water | 51.5% | 52.5% | 48.2% |
| | Cocamide DEA[4] | 3.0% | 3.0% | 3.0% |
| Phase C | Cocamidopropyl Betaine[5] | 7.0% | 7.0% | 7.0% |
| | Silicone Emulsion[6] | 6.7% | 5.7% | 10.0% |
| Phase D | Deionized Water | q.s. | q.s. | q.s. |
| | Phenoxyethanol and Methylisothiazolinone | 0.5% | 0.5% | 0.5% |

[1]UCARE Polymer JR-30M available from Dow Chemical
[2]Standapol ES-3 ® available from Cognis Corp.
[3]Crothix ® available from Croda Inc.
[4]Monamid 705 ® available from Croda Inc.
[5]Monateric CAB-LC ® available from Croda Inc.
[6]Silicone Emulsion, 2% active silicone level
7. Neolone PE available from Dow Chemical Deionized water is added to the mixing vessel. In order to keep the active silicone loading constant throughout testing, it is necessary to adjust the water level added depending on the percent active silicone in the various emulsions used. With moderate agitation, the polyquaternium-10 is dispersed until fully dissolved and sodium lauryl ether sulfate added. This is then heated to 75° C. and the PEG-150 pentaerythrityl tetrastearate is added with continual mixing. Heat is decreased to 40° C. and cocamide DEA and cocamidopropyl betaine are added. When completely incorporated, silicone microemulsion is added to the base shampoo. The shampoo is mixed for 5-10 minutes and then phenoxyethanol and methylisothiazolinone is added. The water loss is compensated for and the formulation is mixed for an additional 5 minutes. The final pH of the shampoo formulations are approximately 5.5-6.0.

The viscosity of each shampoo was measured using a Helipath viscometer (spindle 93 at 50 rpm) and the results show less of an impact on viscosity for the shampoos containing the silicone polyether functional microemulsions. The transparency of each shampoo formulation was noted by visual observation and the results showed similar to improved transparency with the shampoos containing the silicone polyether functional microemulsions. See Table 11.

TABLE 11

| Sample | Viscosity (cP) | Transparency |
|---|---|---|
| U | 17640 | almost clear |
| V | 8180 | hazy |
| 1872 Emulsion | 7100 | almost clear |

The results of INSTRON WET COMBING using shampoos from Table 10 are shown in Table 12. The results show that all both of the silicone polyether functional microemulsion containing shampoos of the present invention provided a reduction in wet combing force. The shampoos containing the silicone polyether functional microemulsion emulsions were similar in performance to the XIAMETER® MEM-1872 Emulsion containing shampoo. The shampoos containing the silicone polyether functional containing microemulsions of the present invention are therefore capable of significantly improving the wet conditioning properties of hair.

The results of INSTRON DRY COMBING using shampoos from Table 10 are shown in Table 12. The results show that both of the silicone polyether functional microemulsion containing shampoos of the present invention provided a reduction in dry combing force. The shampoos containing the silicone polyether functional microemulsion emulsions were similar in performance to the XIAMETER® MEM-1872 Emulsion containing shampoo. The shampoos containing the silicone polyether functional containing microemulsions of the present invention are therefore capable of significantly improving the dry conditioning properties of hair.

TABLE 12

| | % Wet Reduction | % Dry Reduction |
|---|---|---|
| U | 84.5 | 25.5 |
| V | 83.6 | 37.0 |
| 1872 Emulsion | 84.2 | 20.6 |

Example 6

Rinse-Off Conditioner

TABLE 13

| Ingredient | Weight Percent |
|---|---|
| Deionized Water | q.s. to 100% |
| Cetrimonium Chloride[1] | 0.3 |
| Hydroxyethylcellulose[2] | 1.5 |
| Cetearyl Alcohol[3] | 1.0 |
| PEG-100 Stearate & | 1.0 |

TABLE 13-continued

| Ingredient | Weight Percent |
|---|---|
| Glyceryl Stearate[4] | |
| Silicone Microemulsion from Emulsion U[5] | 6.7 |
| DMDM Hydantoin[6] | 0.2 |

[1]Arquad PC 16-29W available from Akzo Nobel Global Personal Care
[2]Natrosol ® 250 HHR available Ashland Aqualon Functional Ingredients
[3]Crodocol CS-50 ® available from Croda Inc.
[4]Arlacel ® 165 available from Uniqema
[5]Silicone Emulsion, 2% active silicone level
[6]Glydant ® available from Lonza, Inc.

Deionized water is added to the mixing vessel and heated to 75° C. With moderate agitation, the hydroxyethyl cellulose is dispersed until fully dissolved. Heat is decreased to 60° C. and cetearyl alcohol and PEG-100 stearate and glyceryl stearate is added. Heat is then decreased to 40° C. and the silicone microemulsion is added to the base conditioner. The conditioner is mixed for 5-10 minutes and then DMDM hydantoin is added. The water loss is compensated for and the formulation is mixed for an additional 5 minutes. The final pH of the conditioner formulations are all approximately 6-7.

Example 7

Leave-in Conditioner

TABLE 14

Leave-in Conditioner

| | Ingredient | Weight % |
|---|---|---|
| Phase A | | |
| 1. | Guar Hydroxypropyltrimonium Chloride[1] | 0.15 |
| 2. | Deionized Water | 60 |
| 3. | Hydroxyethylcellulose[2] | 0.4 |
| Phase B | | |
| 4. | Butylene Glycol | 1 |
| 5. | Glycerin | 3 |
| 6. | Polysorbate 20[3] | 0.3 |
| Phase C | | |
| 7. | Potassium Cetyl Phosphate[4] | 0.05 |
| 8. | Benzophenone-3[5] | 0.3 |
| 9. | EDTA | 0.1 |
| 10. | Deionized Water | 20 |
| Phase D | | |
| 11. | Deionized Water | 7.4 |
| 12. | Silicone microemulsion from Emulsion U[6] | 6.7 |
| 13. | PEG-7 Hydrogenated Castor Oil[7] | 0.3 |
| 14. | DMDM Hydantoin[8] | 0.2 |
| 15. | Sodium Hydroxide (10% solution) | 0.1 |

[1]N-Hance 3196 available from Hercules Inc.
[2]Natrosol Hydroxyethylcellulose available from Ashland Aqualon Functional Ingredients
[3]Tween 20 available from Croda Inc.
[4]Amphisol K available from DSM Nutritional Products, Inc
[5]Escalol 567 available from International Specialty Products
[6]Silicone Emulsion, 2% active silicone level
[7]Croduret 7 available from Croda, Inc.
[8]Glydant ® available from Lonza, Inc.

Add ingredients of Phase A together in mixing vessel. Add phase B to phase A with gentle mixing. Add phase C to AB blend, slowly and with turbulent mixing. Add phase D to mixture (A+B+C). Mix until homogeneous. Adjust the pH with NaOH (10% Solution) to 6-6.5.

Example 8

Conditioning Spray

TABLE 15

Conditioning Spray

| | Ingredient | Weight % |
|---|---|---|
| Phase A | | |
| 1. | Water | 83.5 |
| 2. | EDTA | 0.1 |
| Phase B | | |
| 3. | Polyquaternium-7[1] | 1 |
| 4. | Cocamidopropyl Betaine[2] | 1 |
| 5. | Cetrimonium Chloride[3] | 2 |
| 6. | PEG-8[4] | 1 |
| 7. | Propylene Glycol | 3 |
| 8. | Silicone microemulsion from Emulsion U[5] | 6.7 |
| 9. | Panthenol[6] | 0.5 |
| Phase C | | |
| 10. | Polysorbate 20[7] | 1 |
| 11. | DMDM Hydantoin[8] | 0.2 |

[1]Merquat 550 available from Nalco Company
[2]Monateric CAB-LC ® available from Croda Inc.
[3]Arquad PC 16-29W available from Akzo Nobel Global Personal Care
[4]Polyglykol 400 available from Clariant International Ltd.
[5]Silicone Emulsion, 2% active silicone level
[6]D-Panthenol 75 W available from BASF Corporation
[7]Tween 20 available from Croda, Inc.
[8]Glydant ® available from Lonza, Inc.

Mix Phase A ingredients together until all ingredients are completely dissolved. Add Phase B ingredients to Phase A in order listed. Add Phase C ingredients one at a time in order with mixing. Mix until a homogeneous solution is obtained.

Example 9

Clear Styling Gel

TABLE 16

Clear Styling Gel

| | Ingredient | Weight % |
|---|---|---|
| Phase A | | |
| 1. | Water | 37.5 |
| 2. | VP/VA Copolymer[1] | 2 |
| Phase B | | |
| 3. | Water | 40 |
| 4. | Acrylates Copolymer[2] | 4 |
| 5. | Propylene Glycol | 5 |
| 6. | Triethanolamine | 0.6 |
| 7. | Aloe Vera | 1 |
| Phase C | | |
| 8. | Polysorbate 20[3] | 3 |
| 9. | Silicone Microemulsion from Emulsion U[4] | 6.7 |

TABLE 16-continued

Clear Styling Gel

| | Ingredient | Weight % |
|---|---|---|
| Phase D | | |
| 10. | DMDM Hydantoin[5] | 0.2 |

[1] PVP/VA E-335 available from International Specialty Products
[2] Carbopol ® Aqua SF-1 from Lubrizol
[3] Tween 20 available from Croda, Inc.
[4] Silicone Emulsion, 2% active silicone level
[5] Glydant ® available from Lonza, Inc.

Mix ingredients of Phase A together. Mix ingredients of Phase B together. Add Phase A to Phase B mixing until homogeneous. Mix Phase C and add to Phase AB. Add Phase D ingredient and mix until homogenous.

Example 10

The procedure of Example 2 was repeated except Vitamin E ((+) α-Tocopherol) was mixed with the polydiorganosiloxanepolyoxyalkylene copolymer and then emulsified.

TABLE 17

| MD396D(EO7)4M containing 5% isofol-12 | 30 |
|---|---|
| (+) α-Tocopherol | 1.60 |
| Biosoft EC 690 | 14 |
| H2O #1 | 10 |
| Dilution water | 10 |
| Dilution water | 34.4 |
| Total (wt %) | 100.00 |
| Appearance-final emulsion | clear yellowish microemulsion |
| Dv(0.5) | 45 |
| Dv(0.9) | 87 |
| Oil phase content | 32% |
| Surfactant/oil phase | 42.0% |

Example 11

Clear Shower Gel

TABLE 18

| Phase A | | |
|---|---|---|
| 1. | Water | 42.8 |
| 2. | Carbopol Aqua SF1/NOVEON/Lubrizol | 7.65 |
| 3. | Sodium Lauryl Sulfate | 39 |
| 4. | Sodium Hydroxide (25% solution) | 0 |
| Phase B | | |
| 5. | Cocamidopropyl Betaine | 8 |
| 6. | Disodium EDTA | 0.05 |
| 7. | DMDM Hydatoin | 0.5 |
| Phase C | | |
| 8. | Microemulsion from Example 2 | 2 |
| 9. | Sodium Chloride | 0 |
| | Total (wt %) | 100 |

Procedure
1. Disperse ingredient 2 into the water and mix until uniform.
2. Add ingredient 3 with gentle mixing.
3. Neutralize to pH 6.5 with sodium hydroxide.
4. Add phase B ingredients in the order listed.
5. Add ingredients 8.
6. Add ingredient 9 till desired viscosity is reached.

Example 12 & 13

Clear Toner

TABLE 19

| Example | 12 | 13 |
|---|---|---|
| Water | 70 | 75 |
| Glycerin | 10 | 10 |
| Ethanol | 5 | 0 |
| Microemulsion from Example 2 | 15 | 15 |
| Total (wt %) | 100 | 100 |
| Appearance | Bluish clear | Bluish clear |

Procedure
1. Mix water, glycerin and ethanol.
2. Slowly add SPE microemulsion and gently mix.

The invention claimed is:

1. An aqueous silicone polyether microemulsion consisting of:
   i) at least 20% by weight of a water immiscible dispersed phase comprising:
   A) a polydialkylsiloxane-polyoxyalkylene copolymer having the average formula

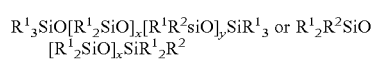
   $R^1_3SiO[R^1_2SiO]_x[R^1R^2SiO]_ySiR^1_3$ or $R^1_2R^2SiO[R^1_2SiO]_xSiR^1_2R^2$ wherein x ranges from 50 to 1000, y ranges from 1 to 50,
   $R^1$ is an alkyl group containing 1 to 6 carbon atoms,
   $R^2$ is a polyoxyalkylene group having the average formula

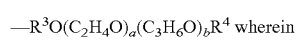
   $—R^3O(C_2H_4O)_a(C_3H_6O)_bR^4$ wherein a is greater than 4, b ranges from 0 to 10,
   $R^3$ is a divalent hydrocarbon group containing 2 to 12 carbon atoms,
   $R^4$ is hydrogen, $R^1$, or an acetyl group,
   with the proviso that the polydialkylsiloxane-polyoxyalkylene copolymer
   contains 0.1 to 10 wt % ethylene oxide ($C_2H_4O$) groups,
   B) optionally, a water immiscible silicone or hydrocarbon fluid, and
   ii) at least 5% by weight of
   C) an emulsifier selected from an anionic surfactant, a cationic surfactant, a nonionic surfactant, or a combination thereof,
   wherein the silicone polyether microemulsion is optically transparent and has an average particle size of less than 100 nanometers.

2. The microemulsion of claim 1 wherein the emulsifier is a surfactant or combination of surfactants capable of forming bi-layer structures when 20-80 wt % of the surfactant is dispersed in water.

3. The microemulsion of claim 2 wherein the formed bi-layer structures are lamellar phase structures.

4. The microemulsion of claim 1 wherein the polydialkylsiloxane-polyoxyalkylene copolymer has the average formula $R^1_3SiO[R^1_2SiO]_x[R^1R^2SiO]_ySiR^1_3$.

5. The microemulsion of claim 4 wherein x is 205 to 500, y is 1 to 20, $R^1$ is methyl, and $R^2$ is —$CH_2CH_2CH_2O[C_2H_4O]_aH$ where a is greater than 4.

6. The microemulsion of claim 1 comprising 40-60 wt % of the water immiscible dispersed phase and 10-40 wt % of C) the emulsifier.

7. A method of making the silicone polyether microemulsion of claim 1 consisting of mixing:
at least 20% by weight of:
A) a polydialkylsiloxane-polyoxyalkylene copolymer having the average formula $R^1_3SiO[R^1_2SiO]_x[R^1R^2SiO]_ySiR^1_3$ or $R^1_2R^2SiO[R^1_2SiO]_xSiR^1_2R^2$ wherein x ranges from 50 to 1000, y ranges from 1 to 50, $R^1$ is an alkyl group containing 1 to 6 carbon atoms, $R^2$ is a polyoxyalkylene group having the average formula —$R^3O(C_2H_4O)_a(C_3H_6O)_bR^4$ wherein a is greater than 4, b ranges from 0 to 10,
$R^3$ is a divalent hydrocarbon group containing 2 to 12 carbon atoms,
$R^4$ is hydrogen, $R^1$, or an acetyl group,
with the proviso that the polydialkylsiloxane-polyoxyalkylene copolymer
contains 0.1 to 10 wt % ethylene oxide ($C_2H_4O$) groups, B) optionally, a water immiscible silicone or hydrocarbon fluid, and at least 5% by weight of
C) an emulsifier selected from an anionic surfactant, a cationic surfactant, a nonionic surfactant, or a combination thereof,
and sufficient water or an aqueous phase to sum to 100% by weight.

8. A method for treating fibers comprising applying to a fiber the microemulsion according to claim 1.

9. The method of claim 8 where the fiber is a hair fiber.

10. The method of claim 9 where the microemulsion is applied to the hair fiber from a personal care product composition.

11. The method of claim 10 where the personal care product composition is a shampoo, leave-on conditioner, rinse-off conditioner, conditioning spray, hair styling spray, hair styling gel, shower gel, or styling composition.

12. A personal care product composition comprising the microemulsion according to claim 1.

13. The personal care product composition of claim 12 where the personal care product is a shampoo, leave-on conditioner, rinse-off conditioner, conditioning spray, hair styling spray, hair styling gel, shower gel, or styling composition.

14. The personal care product composition of claim 13 where the personal care product is a shampoo.

* * * * *